United States Patent
Springer et al.

(10) Patent No.: US 12,144,725 B2
(45) Date of Patent: Nov. 19, 2024

(54) INTRAOCULAR LENS INSERTION SYSTEM

(71) Applicant: Johnson & Johnson Surgical Vision, Inc., Irvine, CA (US)

(72) Inventors: Kevin R. Springer, Santa Ana, CA (US); David A. Ruddocks, Mission Viejo, CA (US); Mark S. Cole, Trabuco Canyon, CA (US); Steven Anderson, Rancho Santa Margarita, CA (US)

(73) Assignee: Johnson & Johnson Surgical Vision, Inc., Irvine, CA (US)

( * ) Notice: Subject to any disclaimer, the term of this patent is extended or adjusted under 35 U.S.C. 154(b) by 173 days.

(21) Appl. No.: 17/822,687

(22) Filed: Aug. 26, 2022

(65) Prior Publication Data

US 2022/0409364 A1    Dec. 29, 2022

Related U.S. Application Data

(63) Continuation of application No. 15/875,732, filed on Jan. 19, 2018, now abandoned.

(51) Int. Cl.
*A61F 2/16* (2006.01)
*A61F 9/007* (2006.01)

(52) U.S. Cl.
CPC .......... *A61F 2/1678* (2013.01); *A61F 2/1613* (2013.01); *A61F 2/1667* (2013.01); *A61F 2/167* (2013.01); *A61F 9/007* (2013.01); *A61F 2/1664* (2013.01); *A61F 2002/1681* (2013.01); *A61F 2/1691* (2013.01); *A61F 2250/0053* (2013.01)

(58) Field of Classification Search
None
See application file for complete search history.

(56) References Cited

U.S. PATENT DOCUMENTS

| | | | |
|---|---|---|---|
| 4,681,102 | A | 7/1987 | Bartell |
| 5,942,277 | A | 8/1999 | Makker et al. |
| 6,685,740 | B2 | 2/2004 | Figueroa et al. |
| 7,156,854 | B2 | 1/2007 | Brown et al. |
| 9,421,092 | B2 | 8/2016 | Brown et al. |
| 2007/0000801 | A1 | 1/2007 | Mauran et al. |

(Continued)

FOREIGN PATENT DOCUMENTS

| | | |
|---|---|---|
| JP | 2007244570 A | 9/2007 |
| JP | 2015228878 A | 12/2015 |

(Continued)

*Primary Examiner* — Brooke Labranche
*Assistant Examiner* — Lindsey Bachman

(57) ABSTRACT

A system for delivering an intraocular lens (IOL) is disclosed, including: a handpiece including a barrel defining an elongate passage, a pushrod disposed inside the elongate passage, and a plunger coupled to the pushrod; and a delivery unit coupled to a first end of the barrel, the delivery unit including a delivery tube and a lens holder coupled to the delivery tube, the lens holder including a lead haptic shelf arranged to receive a lead haptic of an IOL that is contained inside the lens holder, wherein the lead haptic shelf is configured to fold the lead haptic of the IOL over a body of the IOL while permitting the IOL to travel under the lead haptic shelf when the IOL is displaced from the lens holder to the delivery tube by the pushrod during delivery of the IOL into a patient's eye.

14 Claims, 25 Drawing Sheets

(56) References Cited

U.S. PATENT DOCUMENTS

| | | | |
|---|---|---|---|
| 2007/0050023 A1 | 3/2007 | Bessiere et al. | |
| 2008/0058830 A1* | 3/2008 | Cole | A61F 2/1667 606/107 |
| 2008/0086146 A1* | 4/2008 | Ishii | A61F 2/1678 606/107 |
| 2009/0318933 A1* | 12/2009 | Anderson | A61F 2/167 606/107 |
| 2010/0305577 A1 | 12/2010 | Muchhala et al. | |
| 2010/0312254 A1* | 12/2010 | Downer | A61F 2/167 606/107 |
| 2011/0172676 A1 | 7/2011 | Chen | |
| 2014/0257315 A1 | 9/2014 | Wu | |
| 2017/0135811 A1 | 5/2017 | Springer et al. | |
| 2017/0172727 A1* | 6/2017 | Kanner | A61F 2/167 |
| 2017/0354493 A1 | 12/2017 | Andersen et al. | |

FOREIGN PATENT DOCUMENTS

| | | |
|---|---|---|
| WO | 2015168009 A1 | 11/2015 |
| WO | 2016141308 A1 | 9/2016 |

* cited by examiner

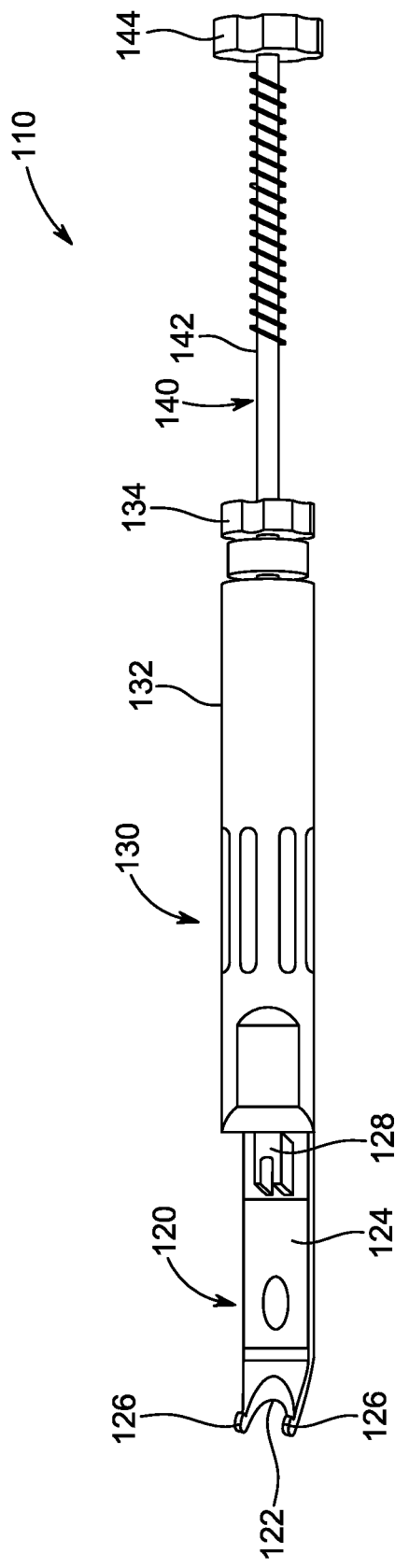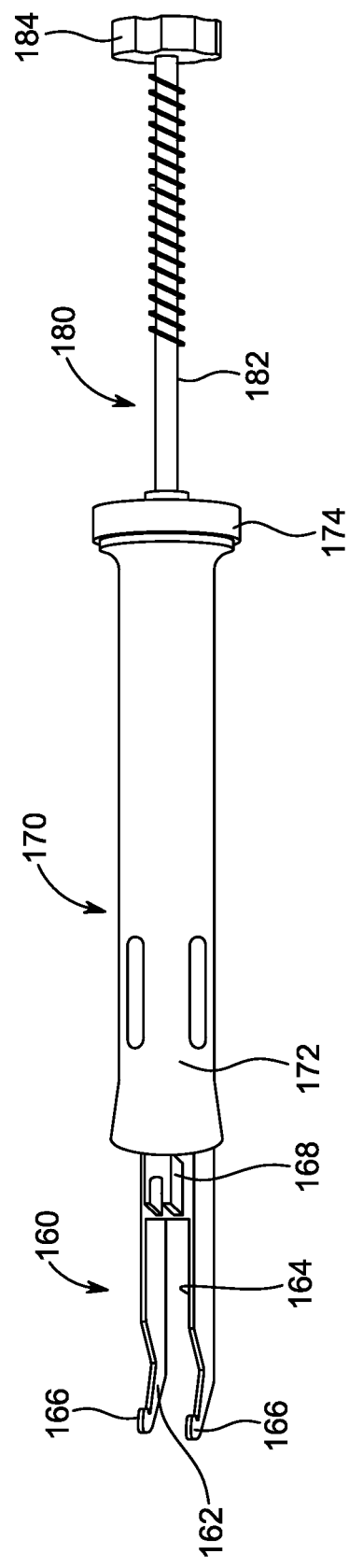
FIG. 1A
FIG. 1B

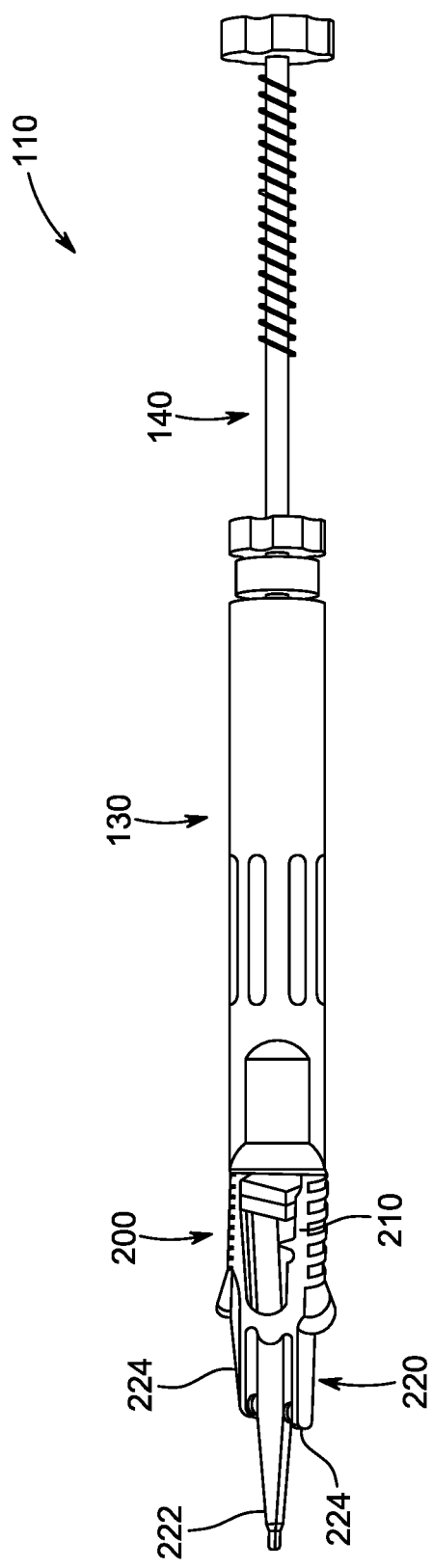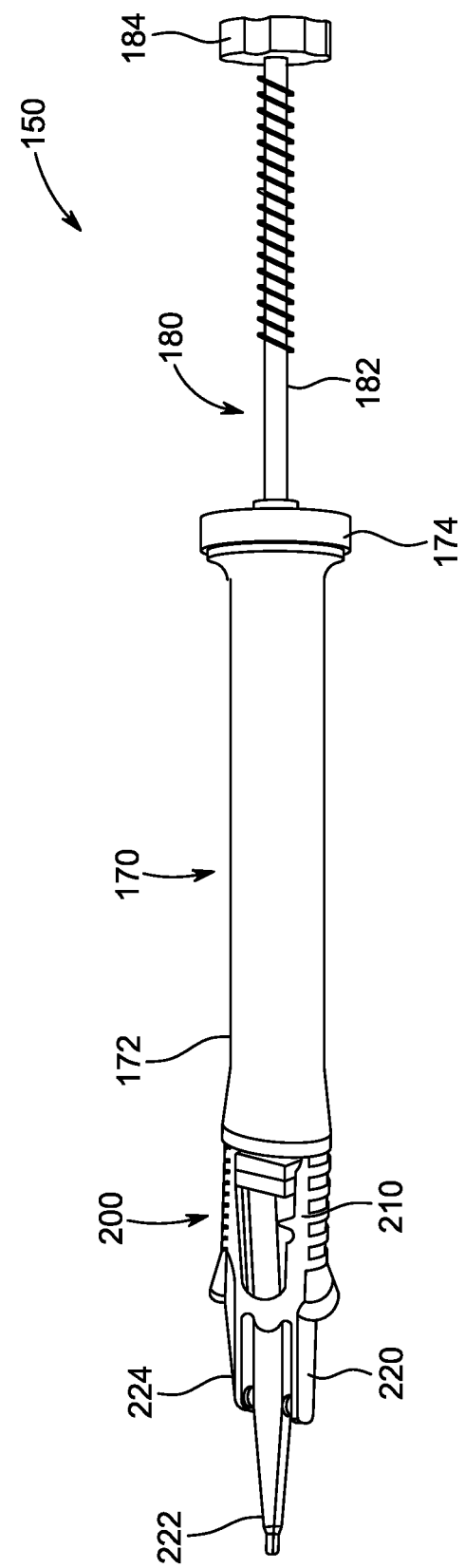

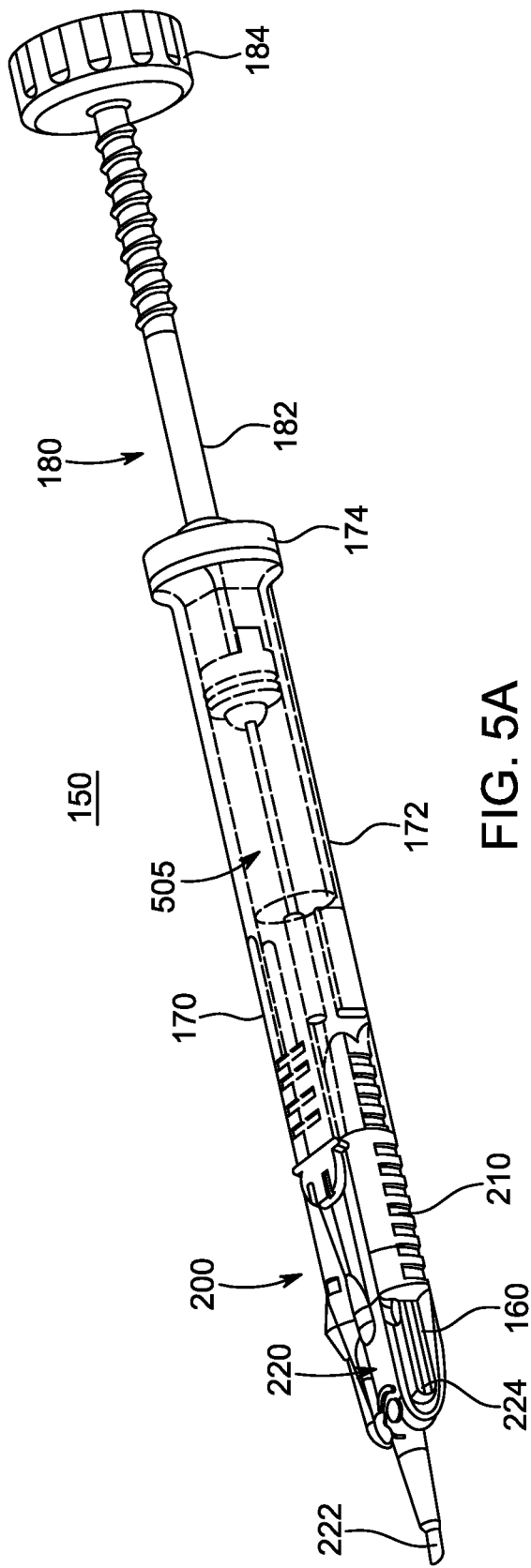
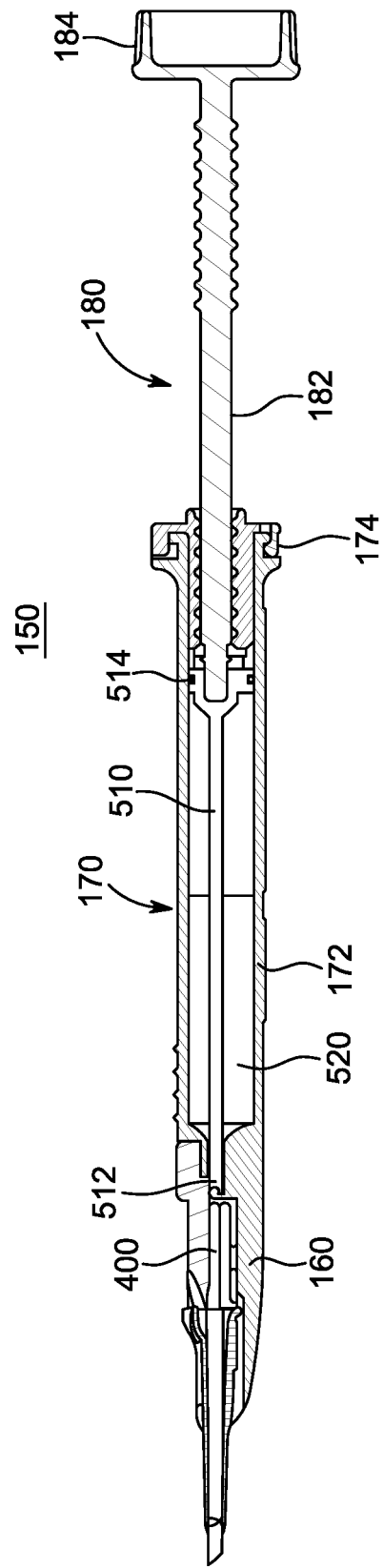
FIG. 5A
FIG. 5B

INTRAOCULAR LENS INSERTION SYSTEM

INCORPORATION BY REFERENCE

This application is a continuation application of U.S. patent application Ser. No. 15/875,732, filed on Jan. 19, 2018, the entire contents of which is incorporated herein by reference as if fully set forth.

FIELD OF INVENTION

The present disclosure relates to devices, methods, and systems for delivering an intraocular lens into an eye. More particularly, the invention relates to devices, systems, and methods in which the intraocular lens is loaded into the front end of the device.

BACKGROUND

It is estimated that 73% of Americans between the ages of 65 to 74 get cataracts. A cataract is a clouding of the eye's lens that impairs a person's vision and, if left untreated, causes blindness. As a result, each year approximately 1.4 million people in the United States alone undergo cataract surgery, whereby the clouded natural crystalline lens is removed and replaced with an intraocular lens (IOL) implant.

Surgeons implant IOLs not only as a replacement for the natural crystalline lens but also to alter the optical properties of (provide vision correction to) an eye in which the natural lens remains. IOLs often include an optically clear disk-like optic of about 6 mm in diameter, and preferably at least one flexible fixation member or haptic which extends radially outward from the optic and becomes affixed in the eye to secure the lens in position.

The optics may be constructed of rigid biocompatible materials such as polymethyl methacrylate (PMMA) or deformable materials such as silicone polymeric materials, acrylic polymeric materials, hydrogel polymeric materials, and the like. The deformable materials allow the IOL to be rolled or folded for insertion through an injector or insertion cartridge and an incision into the eye. Once within the chamber of the eye, the IOL is expulsed from the injector and returns to its original shape.

Injectors or inserters for delivering IOLs into the eye typically employ a delivery device and a removable cartridge that receives the IOL and has a hollow insertion tube or cannula through which the folded IOL is passed using a push rod. Some inserters do without the cartridge. The inserter may be wholly or partly reusable, in which case the inserter or delivery device is usually made of some type of metal alloy that can be sterilized. Alternatively, disposable inserters made of less expensive materials, such as plastics, remain in a sterile package until ready for use. One particularly useful arrangement wherein the cartridge folds over an IOL is disclosed in U.S. Pat. No. 4,681,102 to Bartell. A cartridge opens to receive an IOL in a load chamber, and then folds closed and fits into an injector. A syringe-like plunger in the injector pushes the IOL from the load chamber through a tapered tube into the eye. The IOL unfolds as it emerges from the tip of the tapered tube. Another such insertion system is disclosed in Makker et al., U.S. Pat. No. 5,942,277.

One problem encountered with existing inserters is difficulty in loading the IOL into the inserter or cartridge. The IOL is typically manually moved from a sterile environment to an inserter or associated cartridge using forceps or tweezers. Manual transfer of the IOL presents difficulties in maintaining both sterility of the IOL and the correct orientation of the IOL, especially the haptics, within the cartridge or inserter. A wide variety of performance and outcomes results even with highly skilled personnel, and those having less training are more likely to perform poorly. Improper orientation of the IOL can result in inadequate surgeon control and even damage to the IOL during delivery into the eye.

These problems may be mitigated by preloading the IOL at the manufacturer into a cartridge or container that is designed to be included directly in the inserter. The cartridge or container may be attached to the inserter either at the manufacturer or by the user just prior to surgery. The IOL is stored directly in the inserter in an unstressed state in a sterile package in order to prevent deformation of the optic element. With such configuration, a transfer process would not generally be necessary for loading the IOL into the inserter. One example of storing an IOL in an inserter component is seen in U.S. Pat. No. 7,156,854, filed May 28, 2003. In the '854 patent, a nozzle portion 12 along with a removable stop 26 retains the IOL therein during storage and has internal ramps that assist in folding the IOL optic during an implant procedure. Also, U.S. Patent Publication No. 2008-0058830, filed Jul. 17, 2007, discloses a number of configurations for pre-loading IOLs for transfer to an insertion apparatus, and is expressly incorporated herein.

Despite some advances in this area, there remains a need for devices, systems, and methods that facilitate the placement of IOLs into an inserter or cartridge to reduce the problems associated with manual IOL manipulation.

SUMMARY

The present disclosure addresses this need. According to aspects of the disclosure, a system for delivering an intraocular lens (IOL) is disclosed, including: a handpiece including a barrel defining an elongate passage, a pushrod disposed inside the elongate passage, and a plunger coupled to the pushrod; and a delivery unit coupled to a first end of the barrel, the delivery unit including a delivery tube and a lens holder coupled to the delivery tube, the lens holder including a lead haptic shelf arranged to receive a lead haptic of an IOL that is contained inside the lens holder, wherein the lead haptic shelf is configured to fold the lead haptic of the IOL over a body of the IOL while permitting the IOL to travel under the lead haptic shelf when the IOL is displaced from the lens holder to the delivery tube by the pushrod during delivery of the IOL into a patient's eye.

BRIEF DESCRIPTION OF THE DRAWINGS

The drawings described below are for illustration purposes only. The drawings are not intended to limit the scope of the present disclosure. Like reference characters shown in the figures designate the same parts in the various embodiments.

FIG. 1A is a diagram of an example of a handpiece, according to aspects of the disclosure;

FIG. 1B is a diagram of another example of a handpiece, according to aspects of the disclosure;

FIG. 2A is a diagram of a system for delivering an IOL including the handpiece of FIG. 1A and an IOL delivery unit, according to aspects of the disclosure;

FIG. 2B is a diagram of a system for delivering an IOL including the handpiece of FIG. 1B and an IOL delivery unit, according to aspects of the disclosure;

FIG. 5A is a perspective side view of the system of FIG. 2B, according to aspects of the disclosure;

FIG. 5B is a cross-sectional side view of the system of FIG. 2B, according to aspects of the disclosure;

DETAILED DESCRIPTION

Figure 3A:
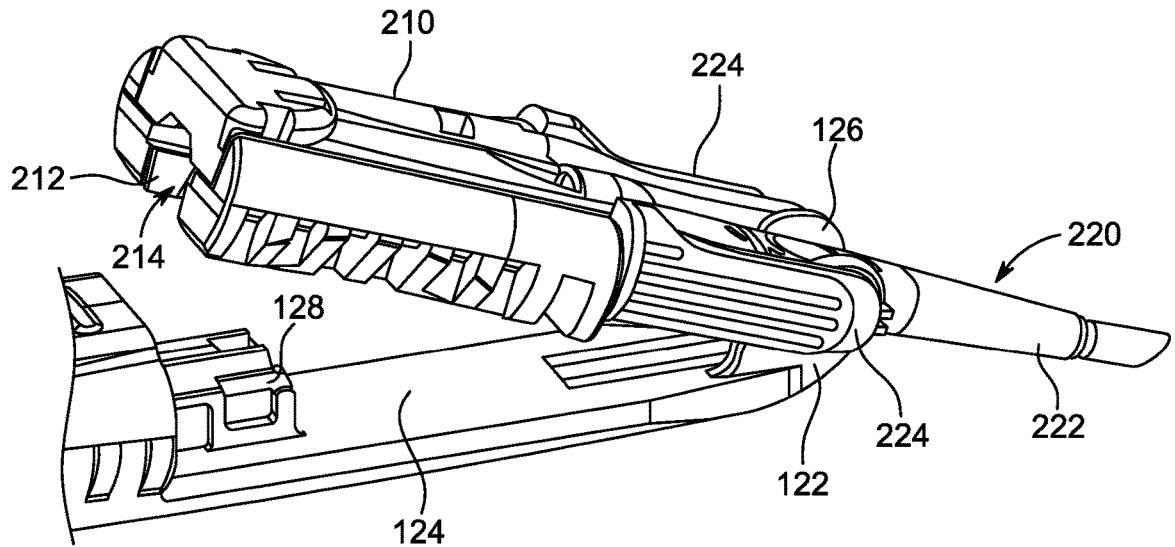
FIG. 3A is a diagram illustrating the manner in which the system of FIG. 2A is assembled, according to aspects of the disclosure.

According to aspects of the disclosure, a system for delivering an intraocular lens (IOL) is disclosed, comprising: a handpiece including a barrel defining an elongate passage, a pushrod disposed inside the elongate passage, and a plunger coupled to the pushrod; and a delivery unit coupled to a first end of the barrel, the delivery unit including a delivery tube and a lens holder coupled to the delivery tube, the lens holder including a lead haptic shelf arranged to receive a lead haptic of an IOL that is contained inside the lens holder, wherein the lead haptic shelf is configured to fold the lead haptic of the IOL over a body of the IOL while permitting the IOL to travel under the lead haptic shelf when the IOL is displaced from the lens holder to the delivery tube by the pushrod during delivery of the IOL into a patient's eye.

According to aspects of the disclosure, a system for delivering an intraocular lens (IOL) is disclosed, comprising: a handpiece including a barrel defining an elongate passage having D-shaped cross-section, a pushrod having a pushrod head disposed inside the elongate passage, and a plunger coupled to the pushrod head, the pushrod head also having a D-shaped cross-section, the pushrod head having an O-ring disposed around a perimeter of the pushrod head; and a delivery unit coupled to the barrel of the handpiece, the delivery unit including a lens holder coupled to a delivery tube, the lens holder having a cavity that is arranged to receive an IOL, the delivery tube being configured to fold the IOL when the IOL is displaced from the lens holder into the delivery tube by the pushrod, wherein the elongate passage includes a first section configured to maintain the O-ring in an uncompressed state when the pushrod head is located in the first section, and a second tapered section configured to compress the O-ring when the pushrod head is displaced from the first section to the second tapered section by the plunger.

According to aspects of the disclosure, a system for delivering an intraocular lens (IOL) is disclosed, comprising: a handpiece including a barrel defining an elongate passage, a pushrod having a pushrod head disposed inside the elongate passage, and a plunger coupled to the pushrod head; a delivery unit coupled to a first end of the barrel, the delivery unit including a lens holder coupled to a delivery tube, the lens holder having a cavity that is arranged to receive an IOL, the delivery tube being configured to fold the IOL when the IOL is displaced from the lens holder into the delivery tube by the pushrod; and a retention nut coupled to a second end of the barrel that is opposite the first end, the retention nut having at least one retention clip that is configured engage the pushrod head to prevent the pushrod from moving while the system is not being used on a patient, the at least one retention clip being further configured to disengage from the pushrod head during normal use of the system on a patient.

According to aspects of the disclosure, a method for selling an intraocular lens (IOL) is provided, comprising: providing an IOL delivery unit that is pre-loaded with an IOL, the IOL delivery unit including a delivery tube and a lens holder coupled to the delivery tube, the lens holder including a cavity inside which the IOL is disposed and a mounting interface for attaching the lens holder to compatible IOL insertion handpieces; providing a first IOL insertion handpiece that is compatible with the IOL delivery unit, the first IOL insertion handpiece including a first barrel defining a first elongate passage, a first pushrod disposed inside the first elongate passage, a first plunger coupled to the first pushrod, and a first receiving interface arranged to receive the IOL delivery unit, wherein the first pushrod is configured to push the IOL through the delivery tube when the IOL delivery unit is mounted in the first receiving interface via the mounting interface and the first plunger is actuated; and providing a second IOL insertion handpiece that is compatible with the IOL delivery unit, the second IOL insertion handpiece including a second barrel defining a second elongate passage, a second pushrod disposed inside the second elongate passage, a second plunger coupled to the second pushrod, and a second receiving interface arranged to receive the IOL delivery unit, wherein the second pushrod is configured to push the IOL through the delivery tube when the IOL delivery unit is mounted in the second receiving interface via the mounting interface and the second plunger is actuated.

According to aspects of the disclosure, a method for selling an intraocular lens (IOL) is provided, comprising: providing a disposable IOL delivery unit that is pre-loaded with an IOL, the IOL delivery unit including a delivery tube and a lens holder coupled to the delivery tube, the lens holder including: (i) a cavity inside which the IOL is disposed and (ii) a mounting interface that is compatible with a plurality of IOL insertion handpieces that are available on the market; and providing a reusable first IOL insertion handpiece that is compatible with the disposable IOL delivery unit, the first IOL insertion handpiece including a first barrel defining a first elongate passage, a first pushrod disposed inside the first elongate passage, a first plunger coupled to the first pushrod, and a first receiving interface arranged to receive the IOL delivery unit, wherein the first pushrod is configured to push the IOL through the delivery tube when the IOL delivery unit is mounted in the first receiving interface via the mounting interface and the first plunger is actuated.

Examples of different systems for delivering an IOL will be described more fully hereinafter with reference to the accompanying drawings. These examples are not mutually exclusive, and features found in one example can be combined with features found in one or more other examples to achieve additional implementations. Accordingly, it will be understood that the examples shown in the accompanying drawings are provided for illustrative purposes only and they are not intended to limit the disclosure in any way. Like numbers refer to like elements throughout.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present invention. As used herein, the term "and/or" includes any and all combinations of one or more of the associated listed items. As used throughout the disclosure the term "distal end" may refer to the end of an IOL delivery system or component thereof, which would be the closest to a patient when the IOL delivery system is used, by an operator, to operate on the patient. As use throughout the disclosure the term "proximal end" may refer to the end of an IOL delivery system or component thereof, which is opposite the distal end, and which would be the closest to the operator when the IOL delivery system is used, by the operator, to operate on the patient.

It will be understood that when an element such as a layer, region or substrate is referred to as being "on" or extending "onto" another element, it can be directly on or extend directly onto the other element or intervening elements may also be present. In contrast, when an element is referred to as being "directly on" or extending "directly onto" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. It will be understood that these terms are intended to encompass different orientations of the element in addition to any orientation depicted in the figures.

Relative terms such as "below" or "above" or "upper" or "lower" or "horizontal" or "vertical" may be used herein to describe a relationship of one element, layer or region to another element, layer or region as illustrated in the figures. It will be understood that these terms are intended to encompass different orientations of the device in addition to the orientation depicted in the figures.

FIG. 1A is a diagram of an example of a handpiece 110, according to aspects of the disclosure. The handpiece 110 includes a cradle 120, a body 130, and a plunger 140. The cradle 120 includes a retention fork 122 and a holding base 124. The retention fork 122 includes a respective hook 126 on each of its prongs and the holding base 124 includes a latch 128 formed at its distal end. The body 130 includes a barrel 132 and retention nut 134 disposed at the proximal end of the barrel. The plunger 140 includes a threaded shaft 142 and a thumb nut 144 disposed at the proximal end of the threaded shaft 142.

FIG. 1B is a diagram of an example of a handpiece 150, according to aspects of the disclosure. The handpiece 150 includes a cradle 160, a body 170, and a plunger 180. The cradle 160 includes a retention fork 162 and a holding base 164. The retention fork 162 includes a respective hook 166 formed at the end each of its prongs and the holding base 164 includes a respective latch 168 formed on its distal end. The body 170 includes a barrel 172 and retention nut 174 disposed at the proximal end of the barrel 172. The plunger 180 includes a threaded plunger shaft 182 and a thumb nut 184 disposed at the proximal end of the plunger shaft 182.

FIG. 2A shows the handpiece 110 with a delivery unit 200 installed in the cradle 120. The delivery unit 200 includes a lens holder 210 and a cartridge 220. The lens holder 210 includes a plurality of latches 212 disposed in a slot 214 (shown in FIG. 3A). The cartridge 220 includes a delivery tube 222 and wing sections 224. As illustrated in FIG. 3A, when the delivery unit 200 is mounted onto the handpiece 110, the delivery unit 200 is placed in the cradle 120 of the handpiece 110 by inserting the distal ends of the wing sections 224 into the hooks 126 and then pressing the delivery unit 200 down until the latches 212 have engaged the latch 128. When the delivery unit 200 is installed in the handpiece 110, the delivery tube 222 of the cartridge 220 is situated between the prongs of the retention fork 122.

Figure 3B:
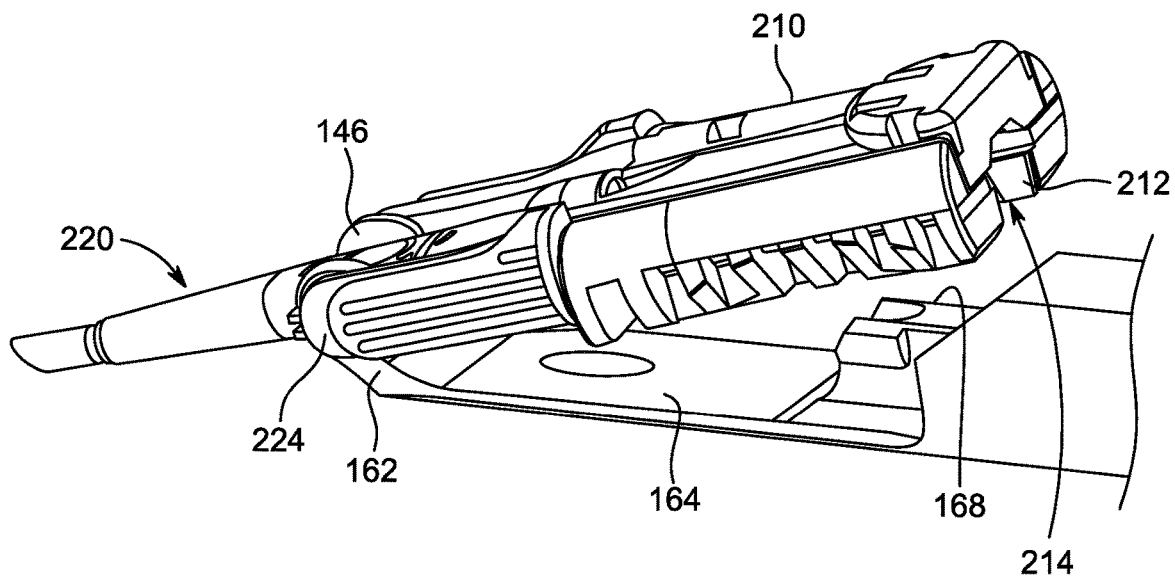
FIG. 3B is a diagram illustrating the manner in which the system of FIG. 2A is assembled, according to aspects of the disclosure.

FIG. 2B shows the handpiece 150 with a delivery unit 200 installed in the cradle 160. As illustrated in FIG. 3B, when the delivery unit 200 is mounted onto the handpiece 150, the delivery unit 200 is placed in the cradle 160 of the handpiece 150 by inserting the distal ends of the wing sections 224 into the hooks 166 and then pressing the delivery unit 200 down until the latches 212 have engaged the latch 168. When the delivery unit 200 is installed in the handpiece 110, the delivery tube 222 of the cartridge 220 is situated between the prongs of the retention fork 162.

The handpieces 110 and 150 are both adapted to receive the same IOL delivery unit, and they may have a similar structural composition. However, in some implementations, the handpiece 110 may be reusable, and the handpiece 150 may be disposable. The handpiece 110 may be formed of titanium, steel, and/or any other durable material. By contrast, the handpiece 150 may be formed of polypropylene and/or another similar material. The handpiece 150 may be pre-loaded with a delivery unit by the manufacturer, and shipped to hospitals and other health management facilities where it can remain in storage until it needs to be used. After the delivery device is used on a patient, it can be discarded at a minimal cost. According to aspects of the disclosure, the handpieces 110 and/or 150 may be ordered separately from the delivery unit so that ophthalmologists can select her/his handpiece to use with the delivery unit. According to aspects of the disclosure, in some implementations, the only difference between the handpieces 110 and 150 may be in the materials used to make each.

Figure 4:
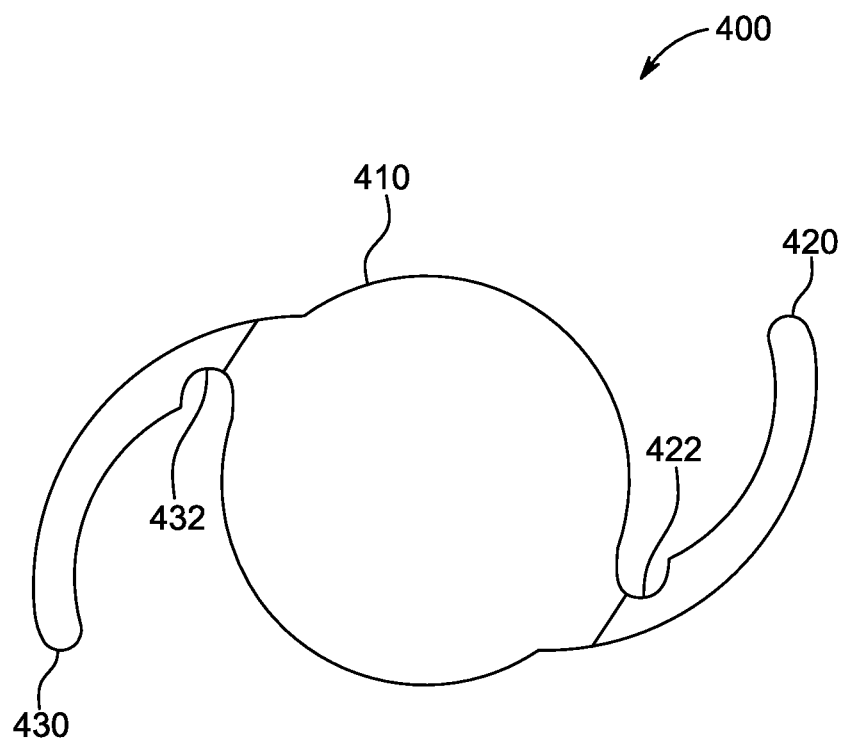
FIG. 4 is a diagram of an example of an IOL, according to aspects of the disclosure.

FIG. 4 is a top-down view of an IOL 400, which can be implanted in the eye of a patient by using any of the handpieces 110 and 150. The IOL includes a body 410, a lead haptic 420 and a trailing haptic 430. The body 410 includes a small plastic lens which can be used to replace or supplement the patient's natural intraocular lens. The haptics 420 and 430 may be small struts that are used to hold the lens in place within the capsular bag inside the patient's eye. The lead haptic 420 is provided with a cutout 422 which permits the lead haptic to fold there when sufficient pressure is applied on the lead haptic 420. The trailing haptic 430 is provided with a cutout 432 which permits the trailing haptic 430 to fold there when sufficient pressure is applied on the trailing haptic 430.

FIGS. 5A-B show the handpiece 150 in further detail. As illustrated in FIG. 5A, the handpiece 150 may be provided with a flat top surface 505 that allows the operator using the handpiece 150 to determine its orientation with or without visual verification. Shown in FIG. 5B is the IOL 400, which is disposed inside the delivery unit 200. Adjacently to the IOL 400, a pushrod 510 is received inside an elongate passage 520 of the barrel 172. The pushrod 510 includes a tip 512 and a pushrod head 514 that is coupled to the plunger shaft 182 of the plunger 180. When the handpiece 150 is used to implant the IOL 400 into the eye of a patient, the pushrod is actuated by the plunger 180, which causes the pushrod 510 to translate axially through the passage 520 and urge the IOL 400 from the lens holder 210, through the delivery tube 222 of the cartridge 220, and into the eye of the patient.

Figure 6:
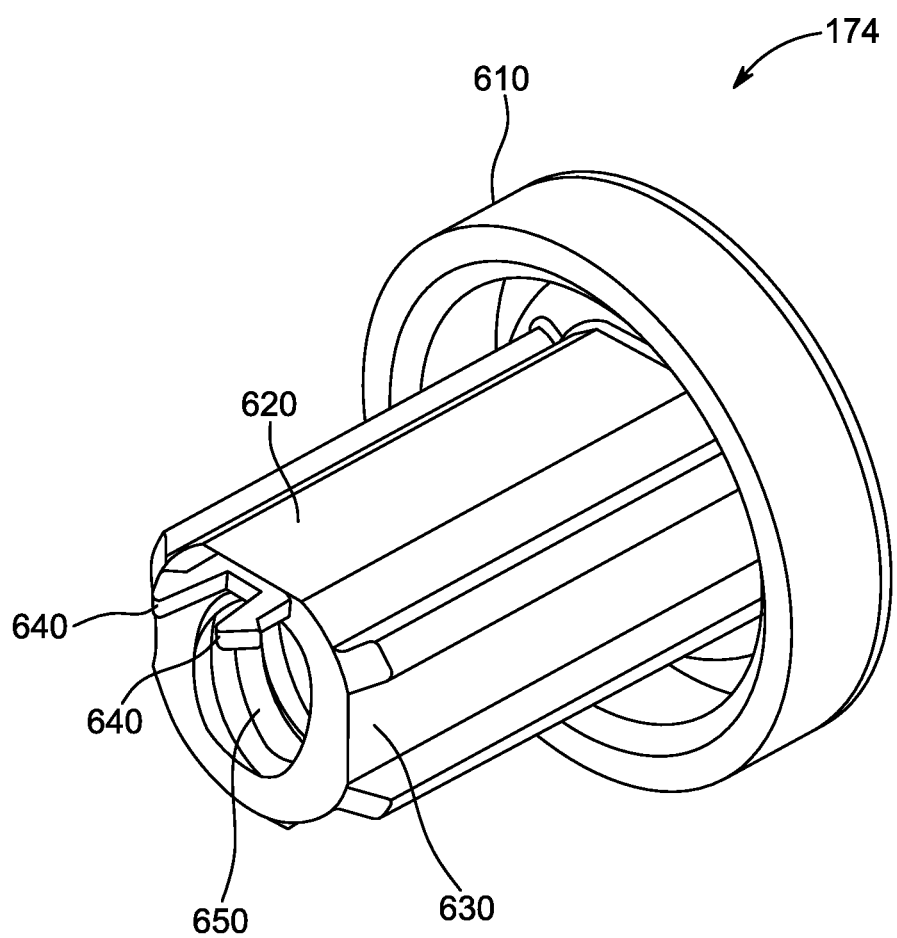
FIG. 6 is a cross-sectional side view of a retention nut of the system of FIG. 2B, according to aspects of the disclosure.

FIG. 6 is a perspective side view of the retention nut 174, according to aspects of the disclosure. As illustrated, the retention nut 174 includes a cap 610, a flat top surface 620, tab guides 630, retention clips 640 formed on the distal end of the retention nut 174, and an interior thread 650. The cap 614 is arranged to engage a lip that is formed on the proximal end of the barrel 172 in order to affix the retention nut 174 to the barrel 172. The flat top surface 620 may be provided to orient the retention nut 174 in the correct position. In some implementations, the flat top surface 620 may also engage a flat interior surface of the passage 520 in order to prevent the retention nut 174 from rotating once the retention nut 174 is installed in the barrel 172. The tab guides 630 are provided to align the pushrod head 514 with the retention nut 174. The retention clips 640 are arranged to engage the pushrod head 514 in order to prevent the pushrod 510 from moving while the handpiece 150 is being transported. The interior thread 650 may be arranged to engage the threads on the threaded plunger shaft 182 of the plunger 180 when the plunger 180 is pushed into the body 170 of the handpiece 150.

Figure 7A:
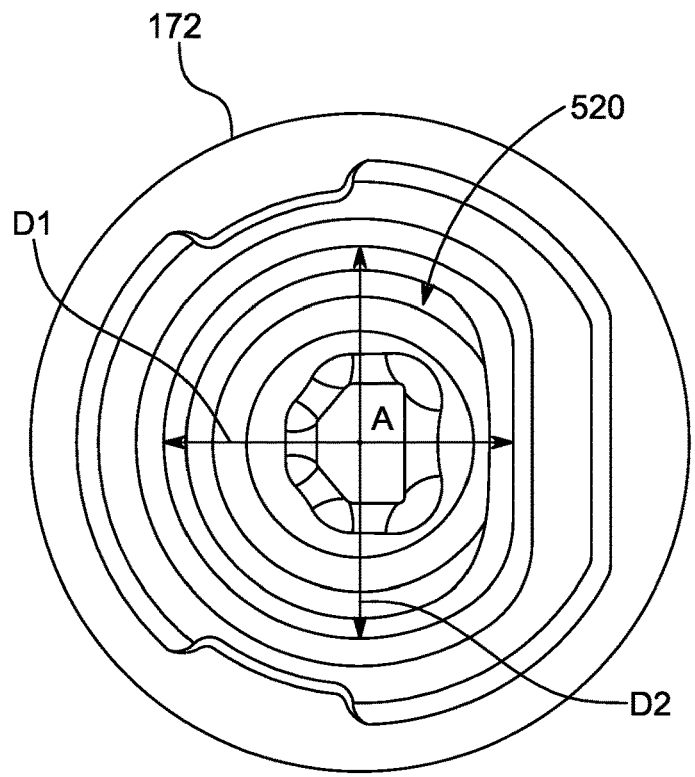
FIG. 7A is a planar view of the proximal end of a barrel of the system of FIG. 2B, according to aspects of the disclosure.
Figure 7B:
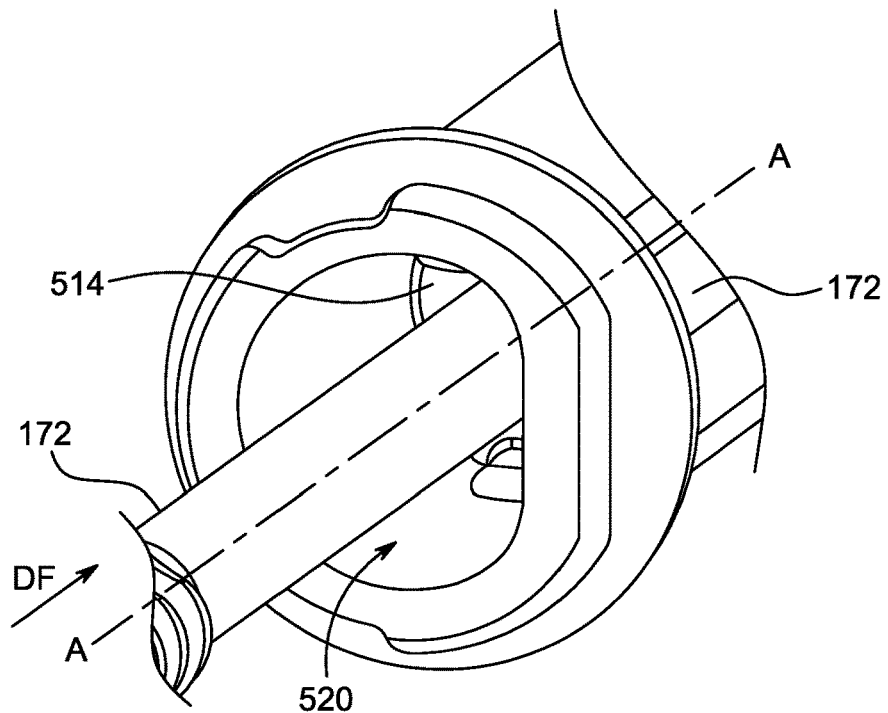
FIG. 7B is a partial view of the system of FIG. 2B, according to aspects of the disclosure.

FIG. 7A is a planar side view of the barrel 172 when viewed from the direction DF and FIG. 7B is a perspective side view of the barrel 172. The direction DF is denoted by the arrow in FIG. 7B. As illustrated, the passage 520 has a D-shaped cross-section characterized by a first diameter D1 and a second diameter D2 that may be greater than or equal to the diameter D1. The passage 520 may have an aspect ratio $A=D2/D1$. In some implementations the aspect ratio A may be equal to or greater than 1. Additionally or alternatively, in some implementations the aspect ratio A may in the range from about 1.0 to about 1.2 or from about 1.0 to about 1.25 or from about 1.0 to about 1.5. As those in the art will appreciate, other aspect ratios may also be appropriate, and the present disclosure is not limited to any particular size for the diameters D1 and D2. For the purposes of these measurements, D2 is measured at the greatest diameter; D1 is measured at the smallest diameter, and the diameter is taken 90 degrees from the flat section, so that the full diameter may be measured.

In some implementations, the passage 520 of the barrel 172 may have a slightly tapered shape. As a result, each of the diameters D1 and D2 may slightly decrease from the proximal end towards the distal end of the barrel 172. For example, the diameter D1 may be larger near the proximal end of the barrel 172 than near the distal end of the barrel 172. Similarly, the diameter D2 may be larger near the proximal end of the barrel 172 than near the distal end of the barrel 172. In other words, the passage 520 may gradually become narrower towards the distal end of the barrel 172.

Figure 7C:
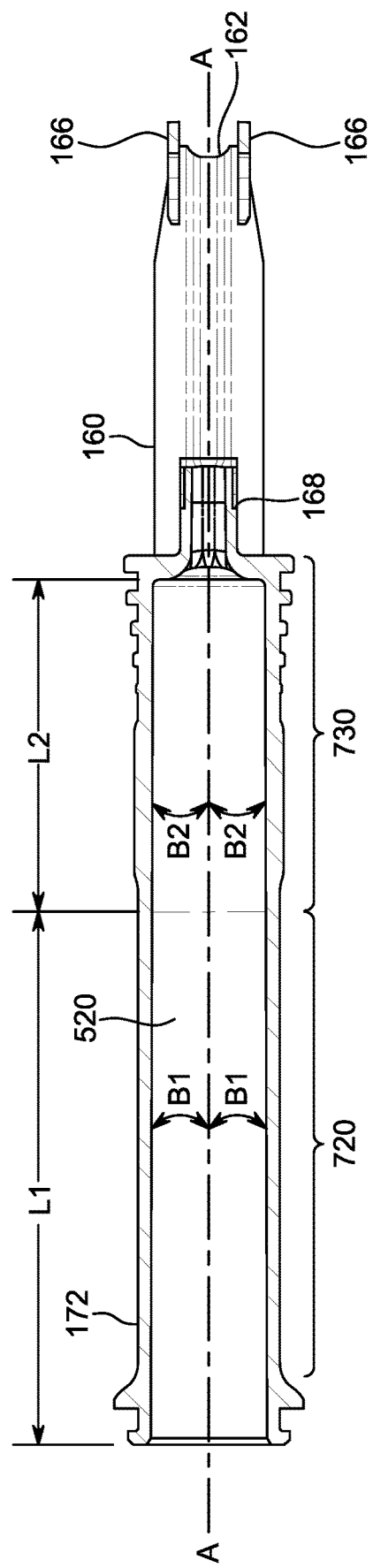
FIG. 7C is a cross-sectional side view of the barrel of the system of FIG. 2B, according to aspects of the disclosure.

FIG. 7C is a cross-sectional view of the barrel 172, according to aspects of the disclosure. As shown, the passage 520 includes a longitudinal axis A-A which runs in the center of the passage 520. Furthermore, the passage 520 includes a first tapered section 720 and a second tapered section 730. The interior walls of the first tapered section 720 of the passage 520 are oriented at an angle B1 relative to the longitudinal axis A-A. The interior walls of the second tapered section 530 are oriented at an angle B2 relative to the longitudinal axis A-A. In some implementations, the angles B1 and B2 may be different from one another. By way of example, the angle B2 may be greater than the angle B1. Additionally or alternatively, in some implementations, the angle B1 may be in the range from about 0.05 or about 0.1 degrees to about 0.1 or about 0.25 or about 0.5 degrees, and the angle B2 may be in the range from about 0.025 or about 0.075 degrees to about 0.15 or about 0.30 or about 0.55 degrees.

Furthermore, in some implementations, the first tapered section 720 may have a length L1 and the second tapered section L2 may have a length L2. In some implementations, the length L1 may be different than the length L2. Additionally or alternatively, in some implementations, the length L1 may be greater than the length L2. Additionally or alternatively, in some implementations, the length L1 may be less than the length L2. Additionally or alternatively, in some implementations, the length L1 may be in the range from about 10 mm to about 30 mm and the length L2 may be in the range of from about 40 mm to about 80 mm. As is further discussed below, the tapered sections 720 and 730 are provided in order to vary the resistance against the movement of the pushrod 510 (or pushrod head 514) when the plunger 180 is depressed, in order to provide better tactile feedback and reduce popping.

Figure 8A:
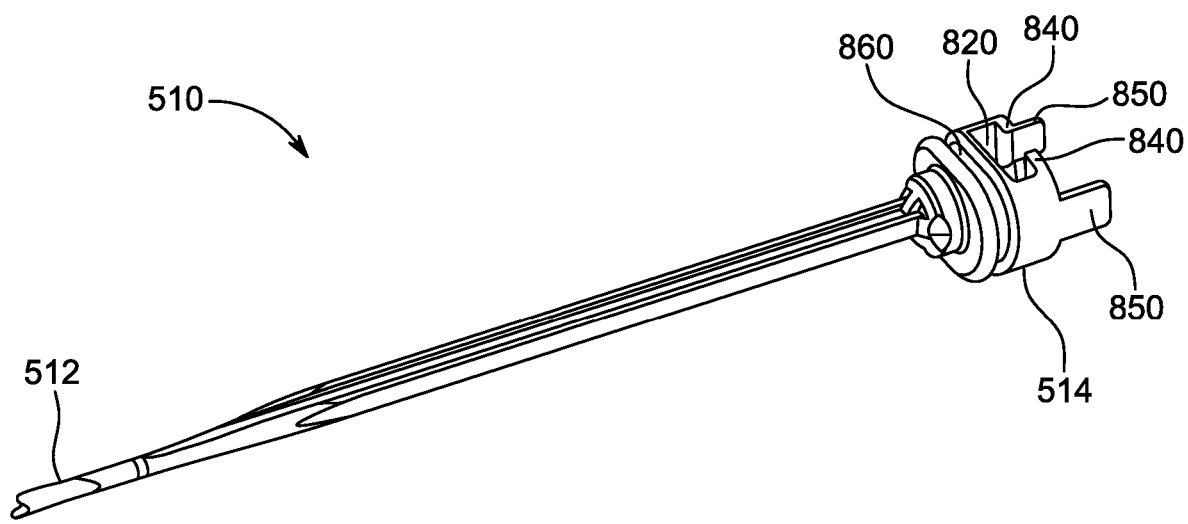
FIG. 8A is a perspective side view of a pushrod of the system of FIG. 2B, according to aspects of the disclosure.
Figure 8B:
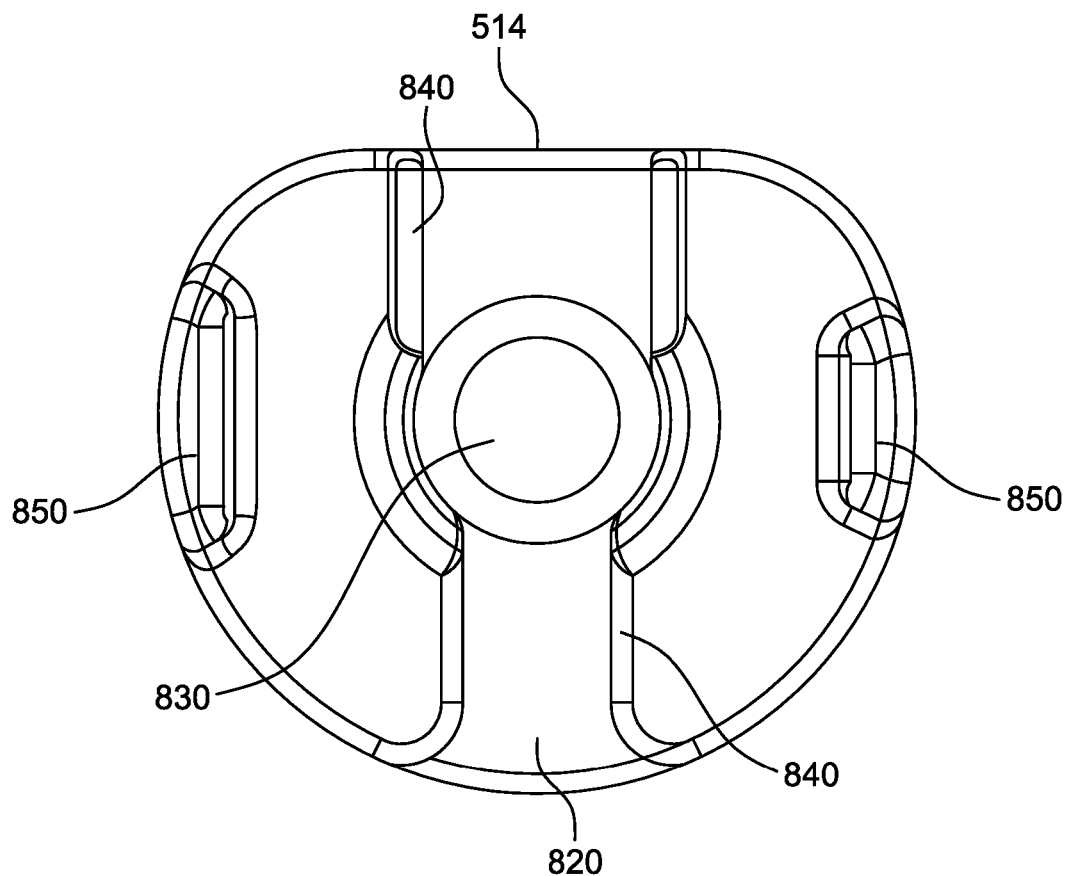
FIG. 8B is a planar side view of a head of the pushrod of FIG. 8A, according to aspects of the disclosure.
Figure 8C:
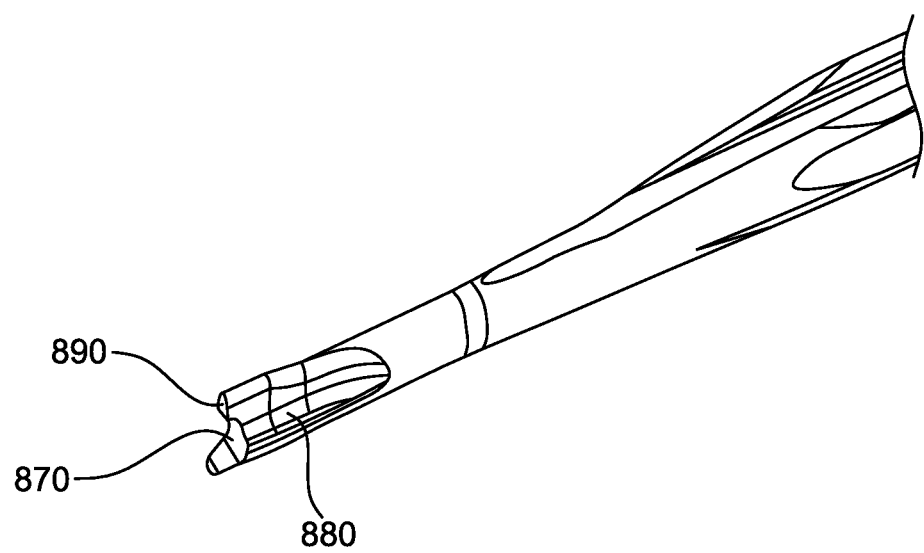
FIG. 8C is partial perspective view of the pushrod of FIG. 8A, according to aspects of the disclosure.
Figure 8D:
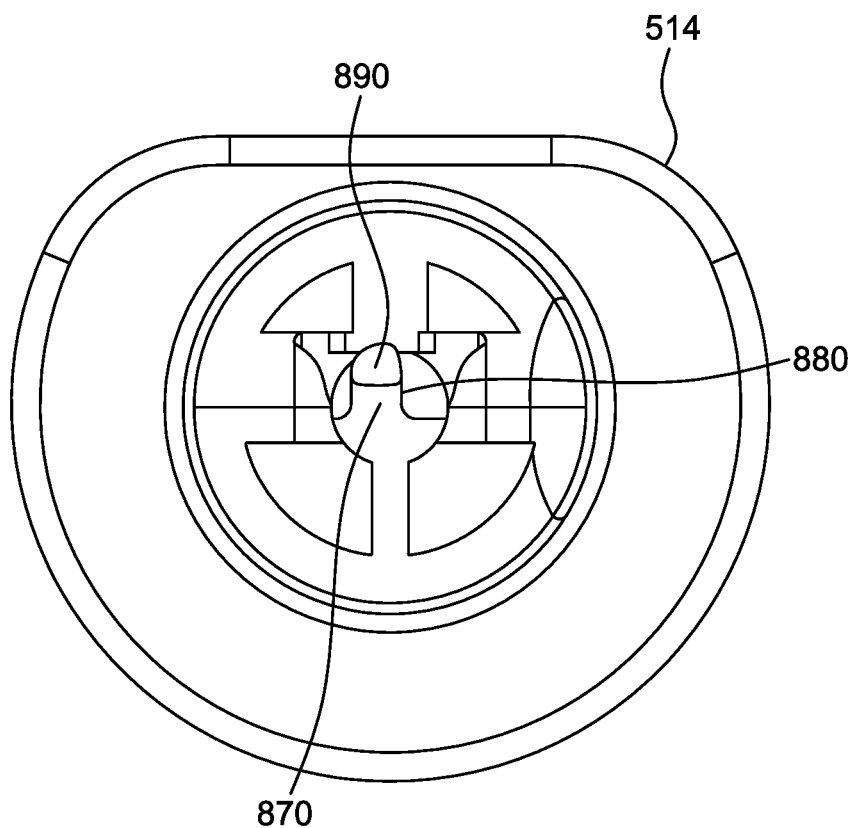
FIG. 8D is a planar side view of a tip of the pushrod of FIG. 8A, when viewed from the distal end of the pushrod, according to aspects of the disclosure.

The pushrod 510 is shown in further detail in FIGS. 8A-D. As illustrated, the pushrod 510 is designed to blend from a round section at the rear of the tip 512 to a rectangular section. The pushrod head 514 includes a recess 820 having a bore 830 formed at the bottom of the recess 820. Lips 840 are overhanging the recess 820 and alignment tabs 850 are provided on the sides of the pushrod head 514. Furthermore, the pushrod 510 includes a channel 860 that is formed around the circumference of the pushrod head 514 to accommodate an O-ring 930 (shown in FIG. 10B). As shown in FIGS. 8C-D, the tip 512 of the pushrod 510 includes a fork 870 and a clearance 880, which is used to accommodate material (e.g., balanced salt solution) that is displaced when the pushrod 510 is actuated. A flat surface 890 is provided on one of the prongs of the fork 870 to engage the trailing haptic 430 when the pushrod 510 is actuated.

Figure 9:
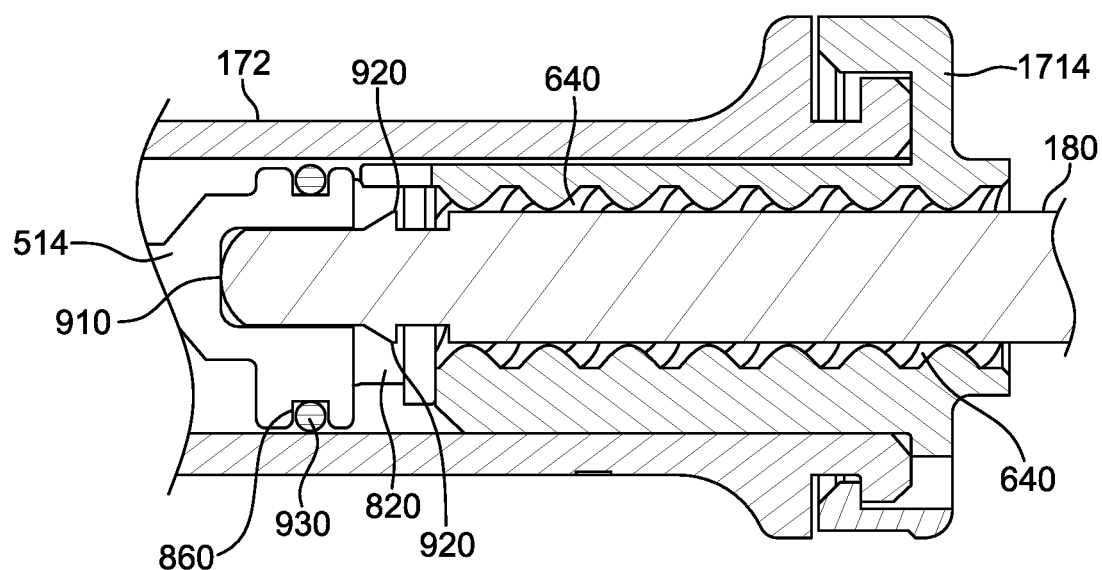
FIG. 9 is a partial cross-sectional side view of the system of FIG. 2B showing the coupling between the pushrod of FIG. 8A and a plunger of the system of FIG. 2B, according to aspects of the disclosure.

FIG. 9 is a cross-sectional side view illustrating an example of a reduced friction joint that is used to connect the plunger 180 to the pushrod 510. As illustrated, the front end 910 of the plunger shaft 182 is inserted into the bore 830 that is formed in the pushrod head 514. When the plunger shaft 182 is inserted into the pushrod head, the arrow snaps 920 compress as they pass through the lip 840 to enter the recess 820 in the pushrod head 514 and expand once they have made it past the lip 840 and into the recess 820 in order to prevent the plunger shaft 182 from being pulled out of the pushrod head 514. As can be readily appreciated, the front end 910 of the plunger shaft 182 may have any suitable type of shape that would permit it to rotate inside the bore 830, such as a spherical shape, a cylindrical shape, etc. In the present example, the front end of the plunger shaft 182 is shaped as a cylinder and is provided with a chamfered edge. In some aspects, inserting the front end 910 of the plunger shaft 182 in the bore 830 may help stabilize the plunger and prevent it from wobbling.

In addition, when the plunger is pushed far enough towards the distal end of the handpiece 150, the thread on the plunger shaft 182 will come in contact with the interior thread 650, which is formed inside the retention nut 174. At this time, the plunger shaft 182 can be screwed into the retention nut 174 to ensure more stable control over the advancement of the pushrod 510 in the final stages of the implantation of the IOL 400. In some implementations, to further stabilize the plunger and prevent it from wobbling, the plunger shaft 182 and the retention nut 174 may be provided with double lead threads that are used to reduce the distance between the thread profiles. The addition of the second lead may provide additional support for the unthreaded length of the plunger, thereby improving the overall stability of operation of the handpiece 150.

Figure 10A:
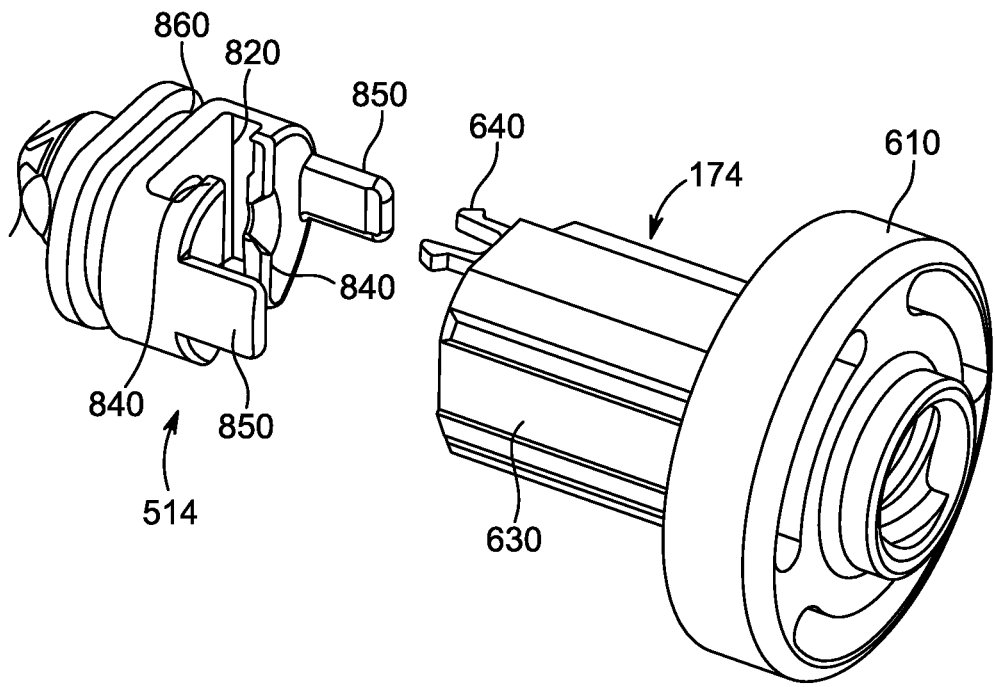
FIG. 10A is a partial perspective view of the pushrod of FIG. 8A and the retention nut of FIG. 6, according to aspects of the disclosure.
Figure 10B:
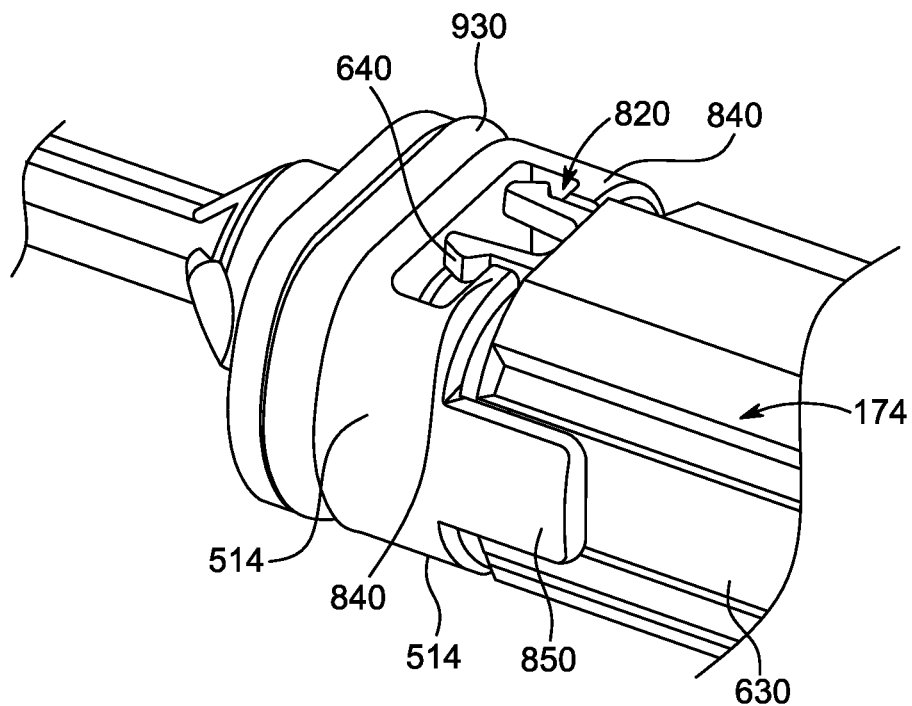
FIG. 10B is a partial perspective view of the pushrod of FIG. 8A and the retention nut of FIG. 6 showing the coupling between the head of the pushrod and the retention nut, according to aspects of the disclosure.
Figure 10C:
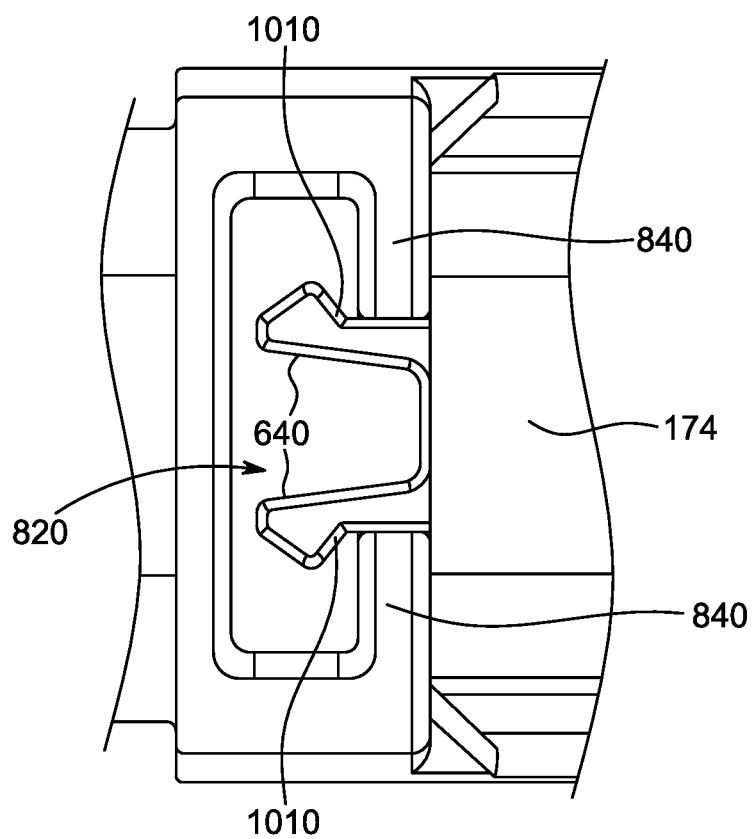
FIG. 10C is a partial perspective top-down view of the pushrod of FIG. 8A and the retention nut of FIG. 6 showing the coupling between the head of the pushrod and the retention nut, according to aspects of the disclosure.

FIGS. 10A-B illustrate the manner in which the pushrod 510 is coupled to the retention nut 174 when the handpiece 150 is held in storage. When the pushrod 510 is coupled to the retention nut 174, the retention clips 640 are received in the recess 820 to prevent the pushrod 510 from accidentally moving when the handpiece 150 is being transported or held in storage. Furthermore, the alignment tabs 850 are received in the tab guides 630, as shown. As can be readily appreciated, the alignment tabs 850 may help orient the pushrod head 514 relative to the retention nut 174, so that the retention clips 640 can snap in place inside the recess 820. FIG. 10C, in particular, shows the manner in which the retention clips 640 engage the lip 840 of the recess 820. As illustrated each retention clip 640 includes a surface 1010 that is arranged at an angle relative to the lip 840. This permits the retention clips 640 disengage from the pushrod head 514 when the plunger 180 is depressed during normal use of the handpiece 150 on a patient. Stated succinctly, the retention clips 640 may increase the dependability of the handpiece 150 by ensuring that the pushrod 510 cannot move unless the plunger 180 is intentionally depressed with a certain amount of force by an operator. This amount of force is greater than the amount of force which the plunger 180 might normally experience as a result of shaking of a package containing the handpiece 150 during storage or transportation.

Also shown in FIGS. 9 and 10B is the O-ring 930, which is disposed in the channel 860 of the pushrod head 512 in order to inhibit the movement of the pushrod 510 inside the passage 520 of the barrel 172. In some aspects, the O-ring 930 may be used to provide a smooth feel during delivery of the IOL 400 in the eye of a patient and prevent the plunger 180 from unwinding during forward rotation of the thumb nut 184. Furthermore, in some implementations, the tapered sections 720 and 730 of the passage 520 may be arranged to engage the O-ring 930 in a manner that is advantageous to the operation of the handpiece 150. More specifically, the first tapered section 720 of the passage 520 may be arranged to allow the O-ring 930 to remain uncompressed when the handpiece 150 is in storage (e.g., when the pushrod head 514 is coupled to the retention nut 174), in order to prevent the O-ring 930 from taking a set shape (while the handpiece 150 is in storage). The second tapered section 730, on the other hand, may be arranged to compress the O-ring in order to cause the pushrod 510 to move smoothly inside the passage 520, while also preventing backup of the pushrod 510 towards the proximal end of the handpiece 150.

In some aspects, when an operator desires to implant the IOL 400 in the eye of a patient, the operator may depress the plunger 180 until the threads on the plunger shaft 182 reach the interior thread 650 which is formed inside the retention nut 174. Afterwards, the operator may begin screwing the plunger 180 into the retention nut 173 by turning the thumb nut 184. Doing so may cause the plunger to advance gradually forward towards the distal end of the handpiece 150. In some aspects, the ability to screw the plunger 180 into the retention nut 174 affords the operator greater precision and control over the rate at which plunger is advanced. This in turn increases the safety of the device with respect to the patient and makes it easier to operate.

As noted above, the plunger performs two types of movements in the forward direction: (i) a translation movement and a (ii) rotation movement. The pushrod 510, on the other hand, performs only one type of movement—namely, a translation movement. This is made possible by the coupling between the pushrod and the plunger (shown in FIG. 9), which permits the front end 910 of the plunger 180 to rotate inside to the pushrod head 514. Furthermore, this is made possible by the shape of the pushrod head (shown in FIG. 8B) and the shape of the passage 520 (shown in FIG. 7A) which prevent the pushrod head from rotating inside the barrel. Although in the present example, both the pushrod head 514 and the passage 520 have a D-shaped cross-section, alternative implementations are possible in which the pushrod head 514 and/or the passage 520 may have another type of shape that would prevent the pushrod head 514 from turning when inside the passage 520. The present disclosure is thus not limited to any particular type of shape for the pushrod head 514 and/or the passage 520.

Furthermore, it should be noted that both the arrow snaps 920 and the retention clips 640 are received in the recess 820. This is made possible by the recess 820 having an opening that extends along the entire width of the pushrod head 514, which permits the retention clips 640 to engage the lip 840 of the recess 820 near the edge of the pushrod head 514.

Figure 11A:
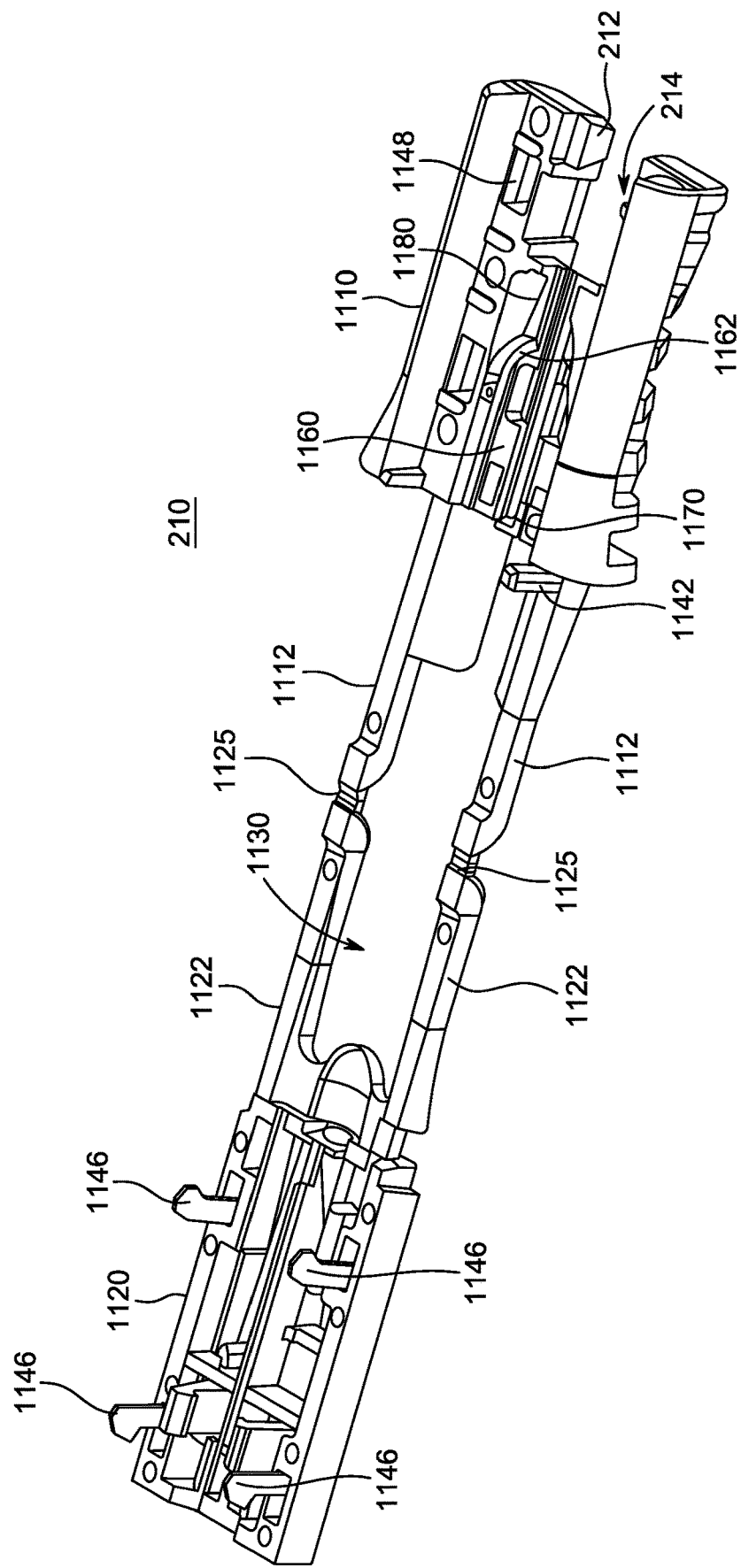
FIG. 11A is a perspective side view of a lens holder, according to aspects of the disclosure.
Figure 11B:
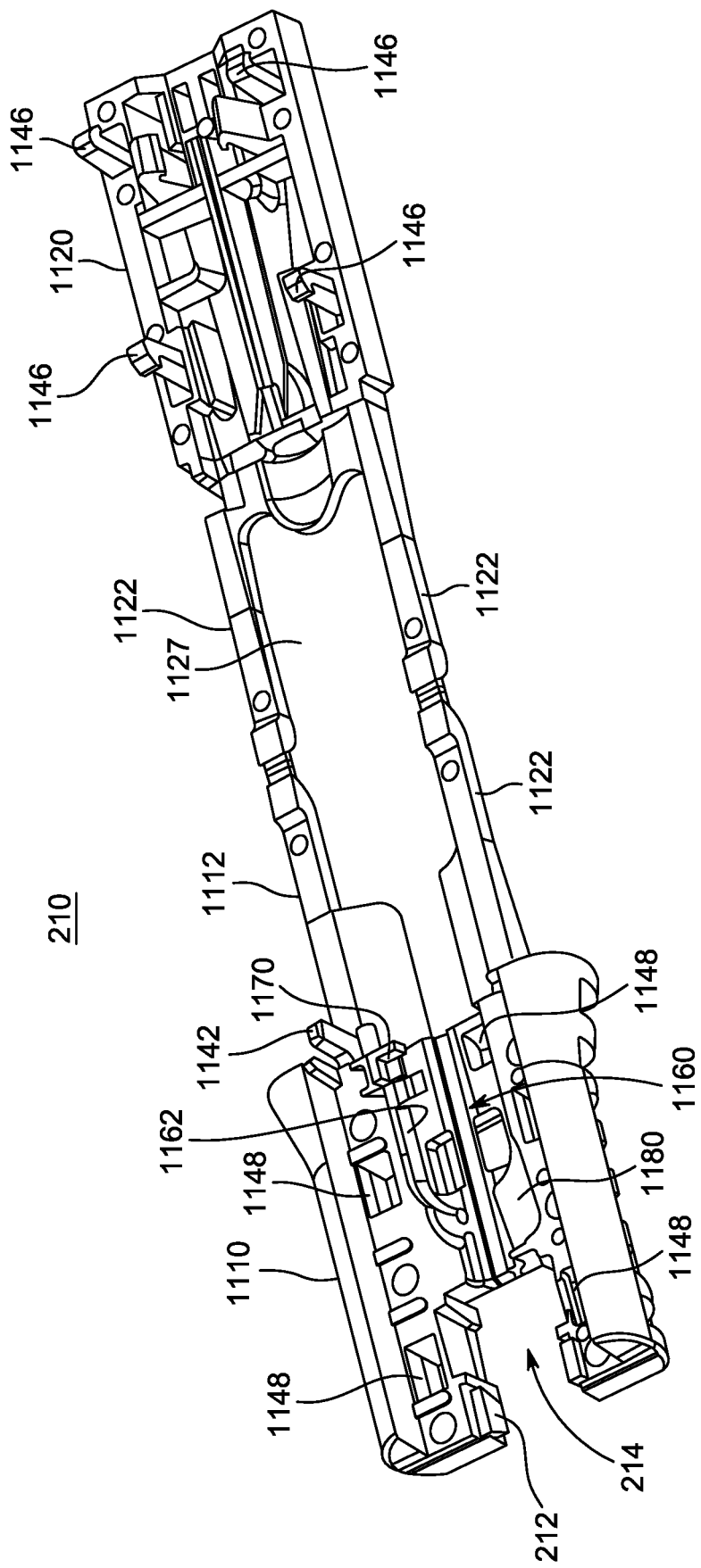
FIG. 11B is another perspective side view of the lens holder of FIG. 11A, according to aspects of the disclosure.

FIGS. 11A-B are perspective top-down views of the of the lens holder 210 when lens holder 210 is open. As illustrated, the lens holder 210 includes a base 1110 and a cover 1120 that are coupled by a pair of living hinges 1125. The base 1110 includes a pair of bifurcated fingers 1112 that meet, at the living hinges 1125, with a similar pair of bifurcated fingers 1122 extending from the cover 1120. The opposed pairs of aligned fingers are shaped so as to form a slot 1130 when folded about the living hinges 1125 for receiving the cartridge 220.

Figure 12A:
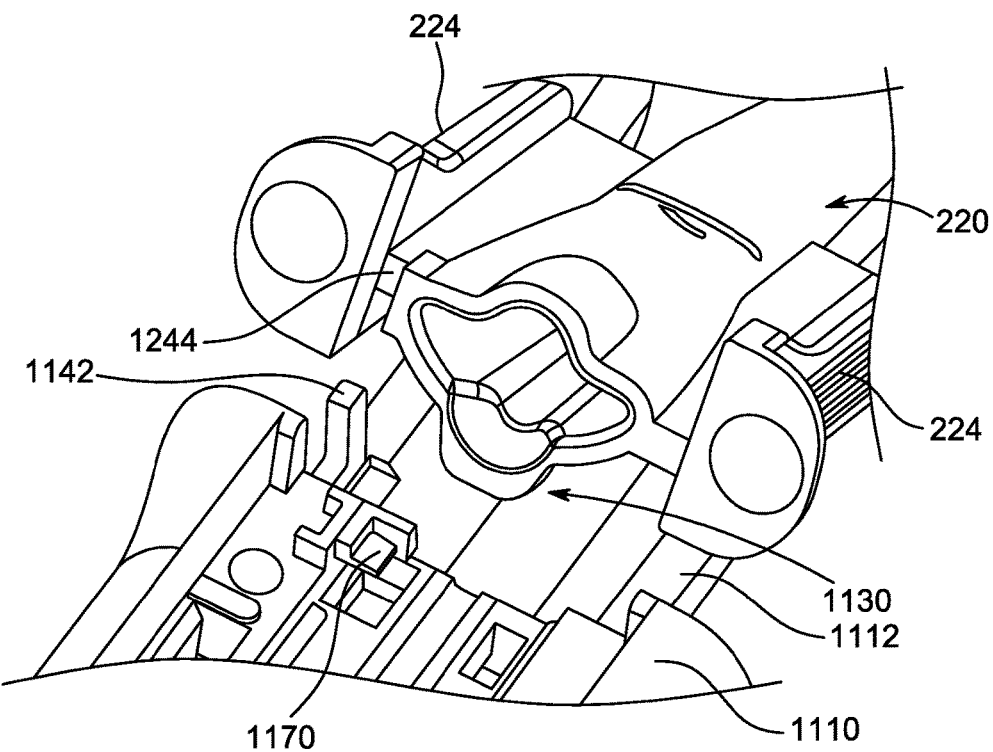
FIG. 12A is a partial perspective view of the lens holder of FIG. 11A showing the manner in which the lens holder is coupled to a delivery cartridge to form an IOL delivery unit, according to aspects of the disclosure.
Figure 12B:
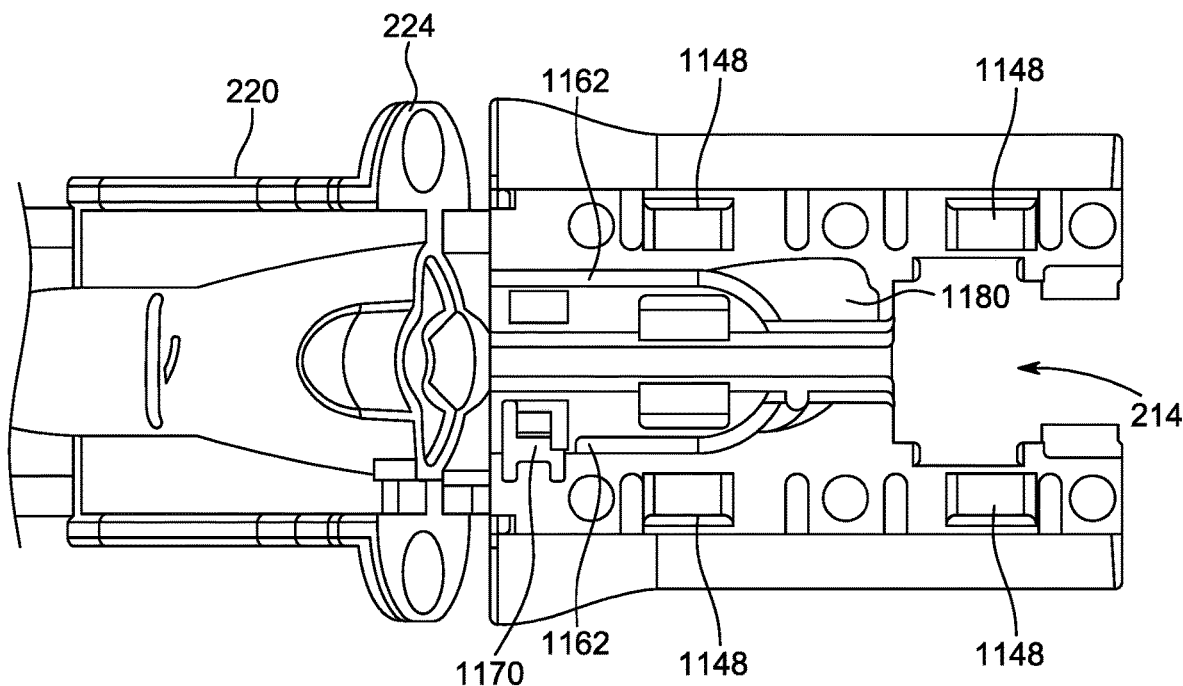
FIG. 12B is a partial top-down view of the lens holder of FIG. 11A showing the manner in which the lens holder is coupled to a delivery cartridge to form an IOL delivery unit, according to aspects of the disclosure.

FIGS. 12A-B show in greater detail how the lens holder 210 and the cartridge 220 are assembled together to form the delivery unit 200. More particularly, the cartridge 220 may be placed in the slot 1130 when the cover 1120 is open, such that an alignment pin 1142 is received in a recess 1244 that is formed in one of the wing sections 224. The alignment pin 1142 and the recess 1244 may prevent the cartridge 220 from being inserted incorrectly while also creating an interference fit that can hold the cartridge 220 in place while the cover 1120 is folded over the base 1110. After the cover 1120 is folded over the base 1110, the latches 1146 are snapped into mating recesses 1148 to lock the base 1110 and the cover 1120 together.

Figure 13:
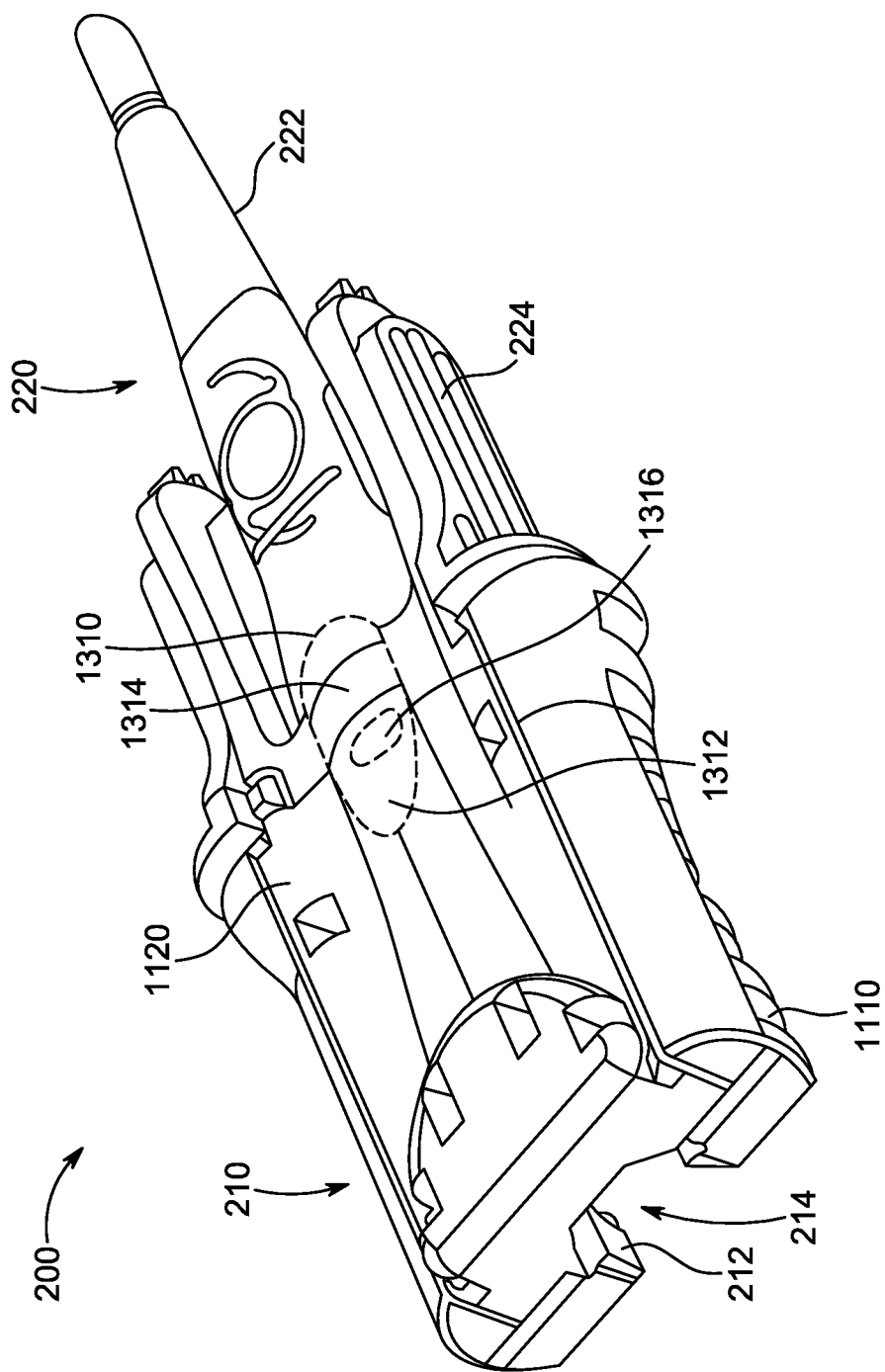
FIG. 13 is perspective side view of a fully assembled IOL delivery unit, according to aspects of the disclosure.

FIG. 13 shows a perspective view of the delivery unit 200 after it is assembled. As illustrated, the delivery unit 200 includes a port 1310, which includes a concave portion 1312, a convex portion 1314, and an opening 1316. According to aspects of the disclosure, the opening 1316 may be used to introduce balanced salt solution (BSS) into the delivery unit 200 in order to keep the IOL 400 lubricated and/or hydrated.

Figure 14:
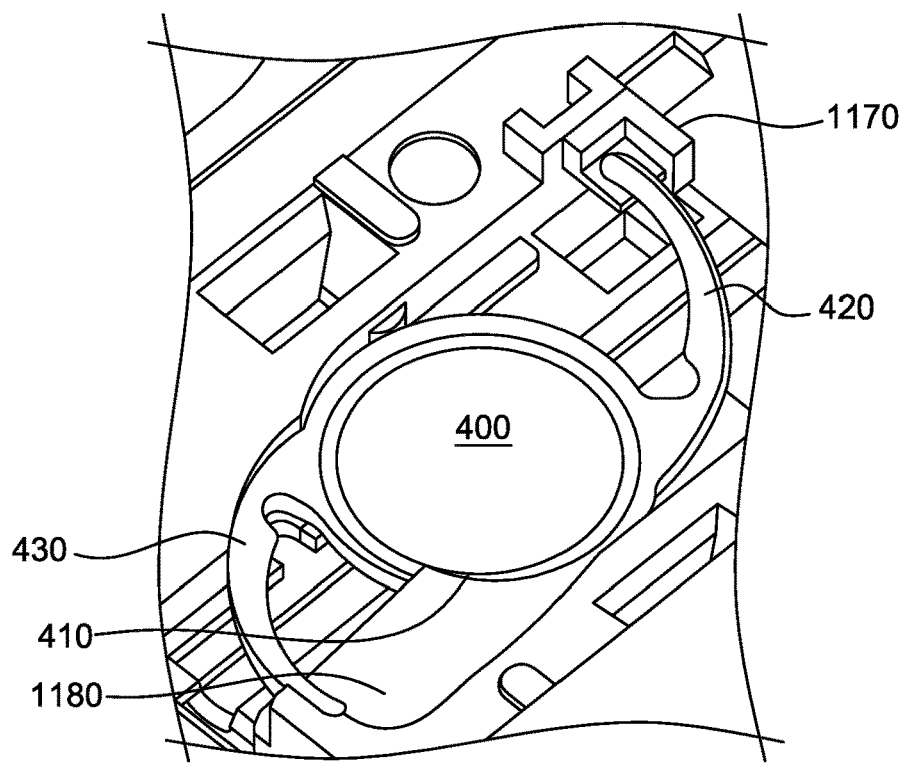
FIG. 14 is a partial top-down cross-sectional view of the IOL delivery unit of FIG. 13 showing the disposition of the IOL of FIG. 4 inside the IOL delivery unit, according to aspects of the disclosure.

Returning to FIGS. 11A-B, the base 1110 includes a cavity 1160 that is arranged to contain the IOL 400. Inside the cavity 1160, a lead haptic shelf 1170 and a trailing haptic shelf 1180 are disposed on opposite sides of the cavity 1160. Furthermore, a ledge 1162 is formed on the sidewalls of the cavity 1160 to provide support for the body 410 of the IOL 400. FIG. 14 is a cross-sectional partial view of the base 1110, which shows the manner in which the IOL 400 is retained within the cavity 1160 of the lens holder 210 prior to the handpiece 150 being used on a patient (e.g., when the handpiece 150 is in storage or being transported from the manufacturer to a healthcare provider). As illustrated, the body 410 of the IOL 400 is rested on the ledge 1162 such that the central portion of the body 410 is suspended above the bottom surface of the cavity 1160 to prevent the central portion of the body 410 from being damaged as a result of coming in contact with the bottom surface of the cavity 1160. The lead haptic 420 is placed on the lead haptic shelf 1170, and the trailing haptic 430 is placed on the trailing haptic shelf 1180.

Figure 15:
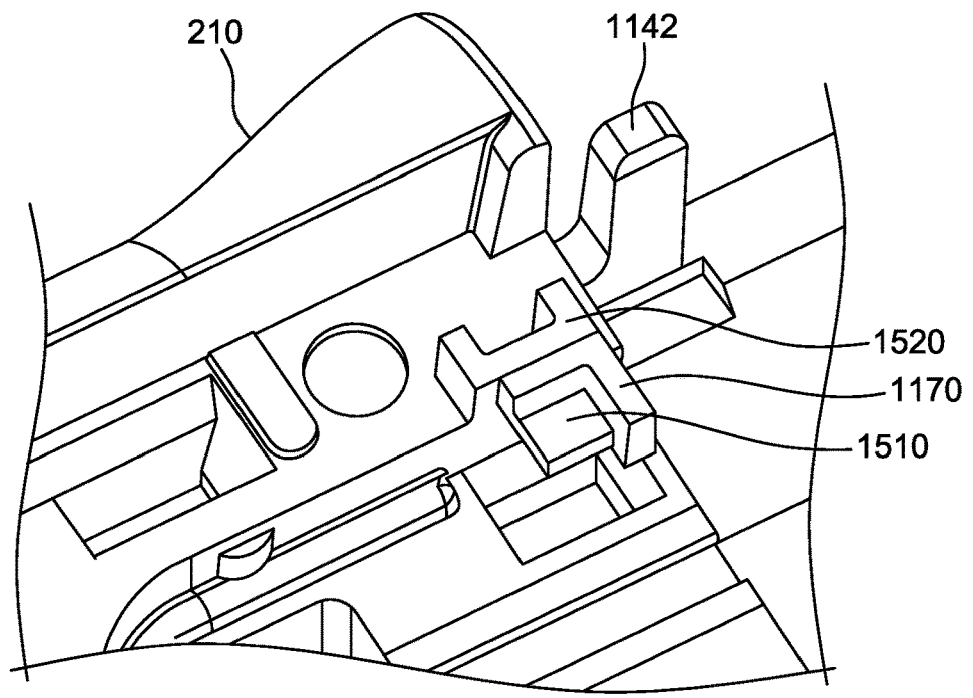
FIG. 15 is a partial top-down cross-sectional view of the IOL delivery unit of FIG. 13 showing a lead haptic shelf of the lens holder on which the lead haptic of the IOL of FIG. 4 is disposed, according to aspects of the disclosure.

FIG. 15 shows the lead haptic shelf 1170 in further detail. The lead haptic shelf includes a base 1510 and a sidewall 1520. When the IOL 400 is placed inside the lens holder 210, the tip of the lead haptic 420 is disposed on the base 1510 and adjacently to the sidewall 1520. In some aspects, this configuration of the lead haptic shelf 1170 is advantageous because it allows the lead haptic 420 of the IOL 400 to be assembled from above without post-assembly haptic manipulation. As is discussed further below, the lead haptic shelf 1170 is used to fold the lead haptic 420 over the body 410 of the IOL 400 when the plunger 180 of the handpiece 150 is depressed.

Figure 16A:
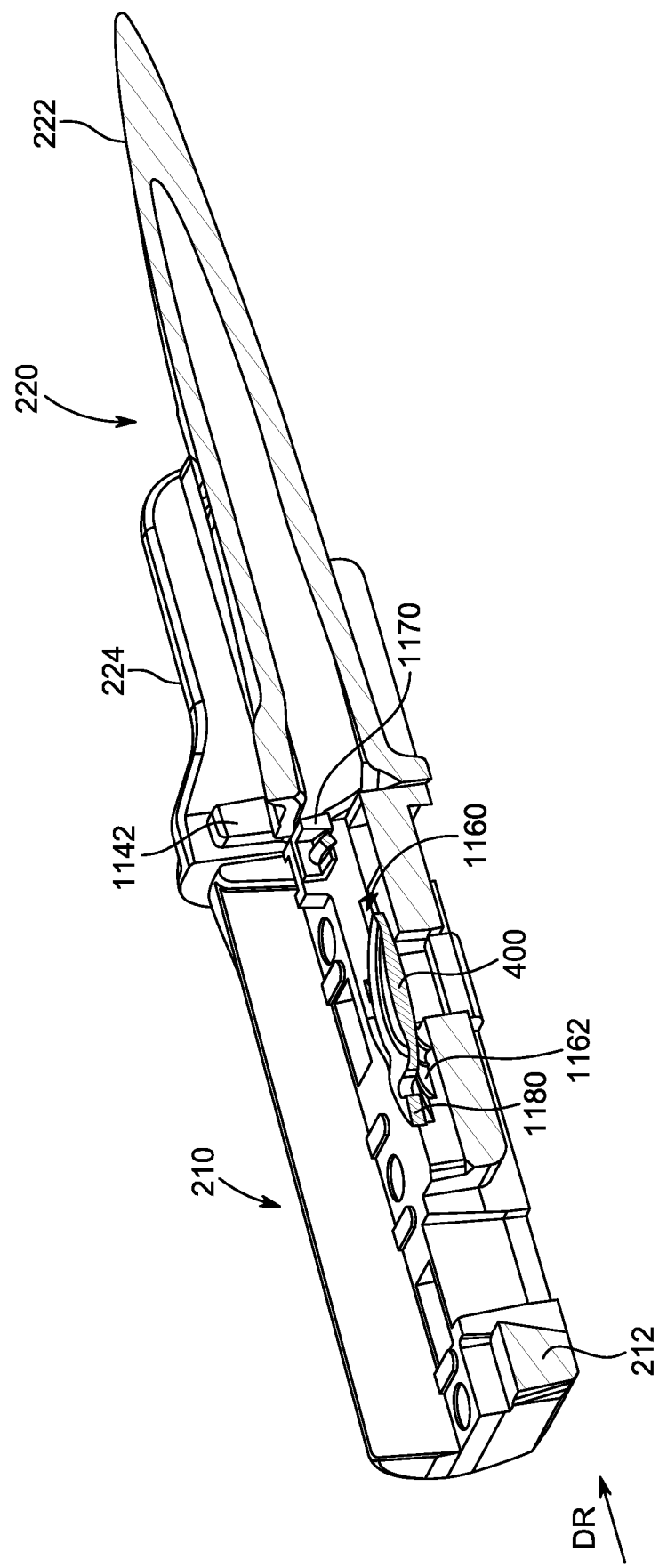
FIG. 16A is a perspective cross-sectional view of the IOL delivery unit of FIG. 13, according to aspects of the disclosure.
Figure 16B:
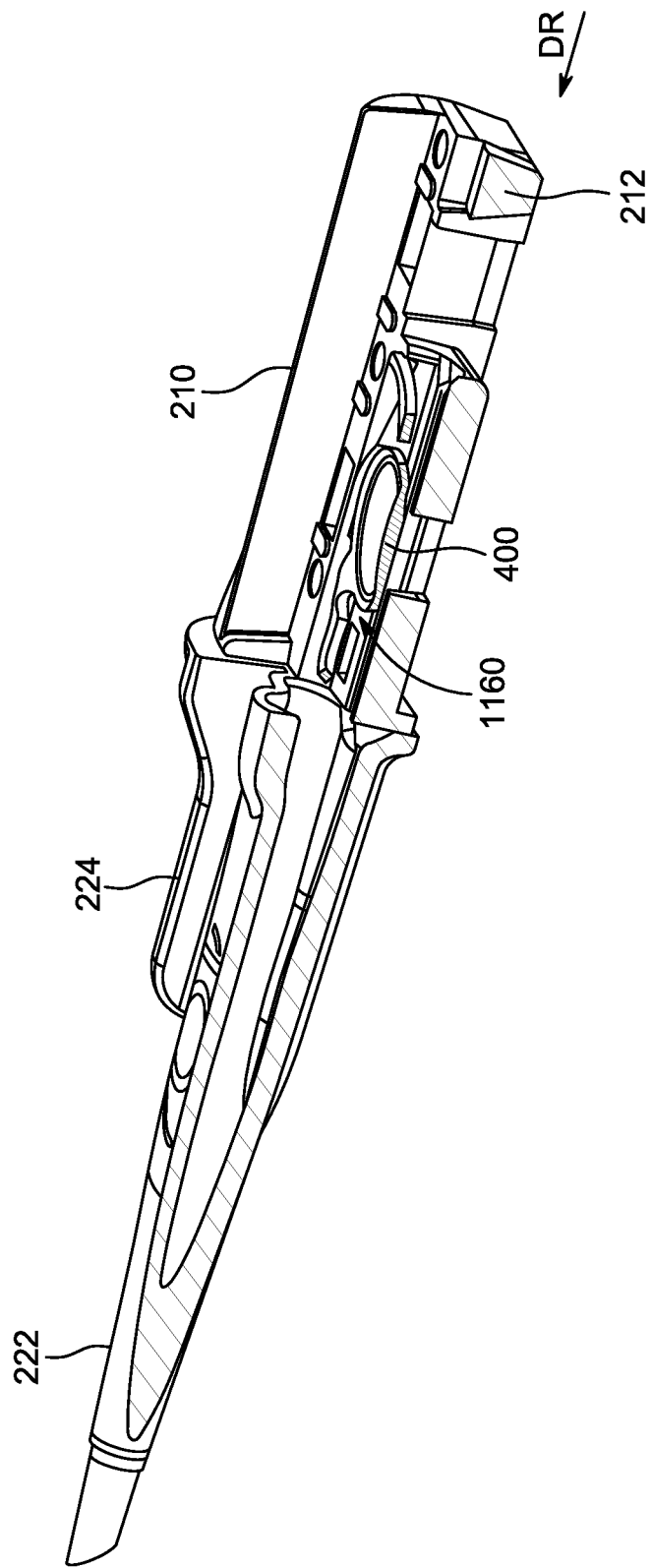
FIG. 16B is a perspective cross-sectional view of the IOL delivery unit of FIG. 13, according to aspects of the disclosure.
Figure 17:
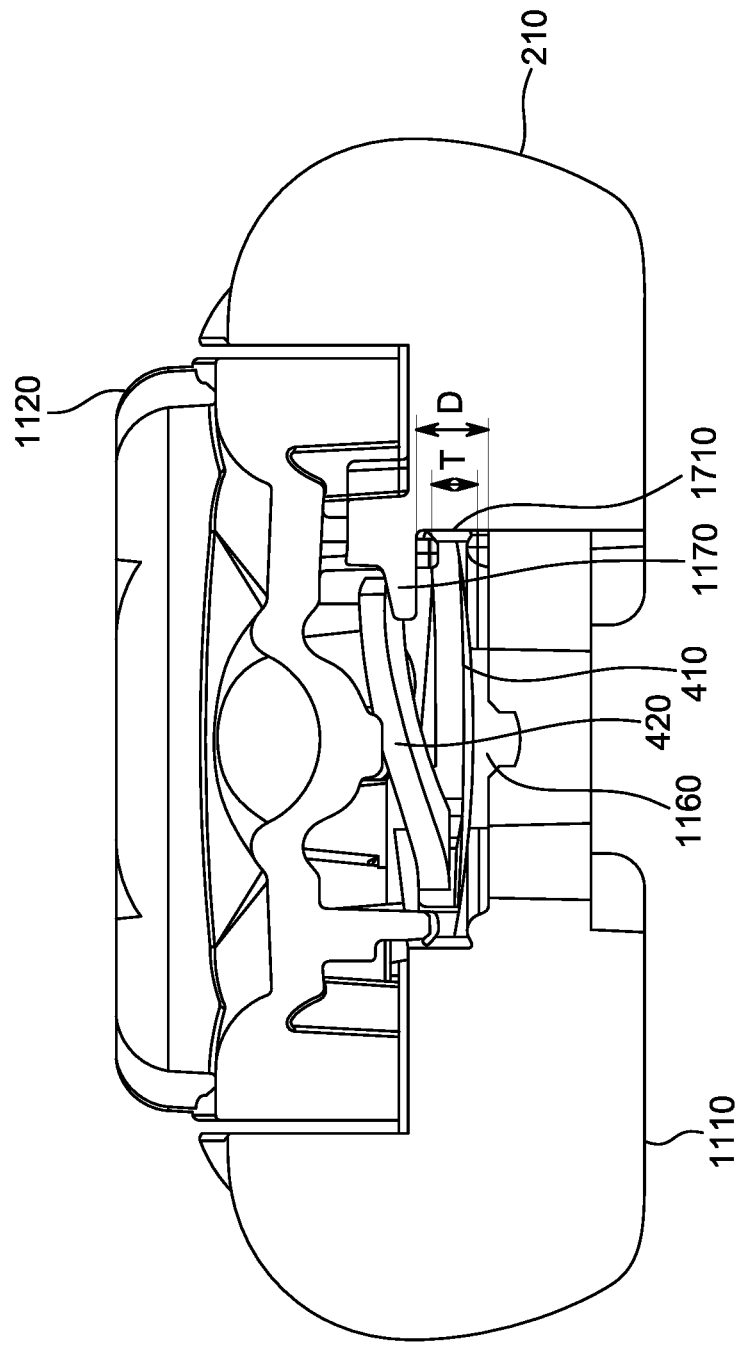
FIG. 17 is cross-sectional side view of the IOL delivery unit of FIG. 13, according to aspects of the disclosure.

FIGS. 16A-B are perspective cross-sectional views of the delivery unit 200. The arrow shown in FIGS. 16A-B denotes direction DR. FIG. 17 is a cross-sectional side view of the delivery unit 200 when viewed from direction DR. FIG. 17 illustrates that the lead haptic shelf 1170 is spaced apart from the bottom of the cavity 1160 by a distance D that is greater than the thickness T of the IOL 400. Furthermore, as shown in FIG. 17, the lead haptic shelf 1170 may overhang the sidewall 1710 of the cavity 1160, thereby permitting the IOL 400 to travel underneath the lead haptic shelf 1170 when the plunger 180 of the handpiece 150 is depressed.

Figure 18A:
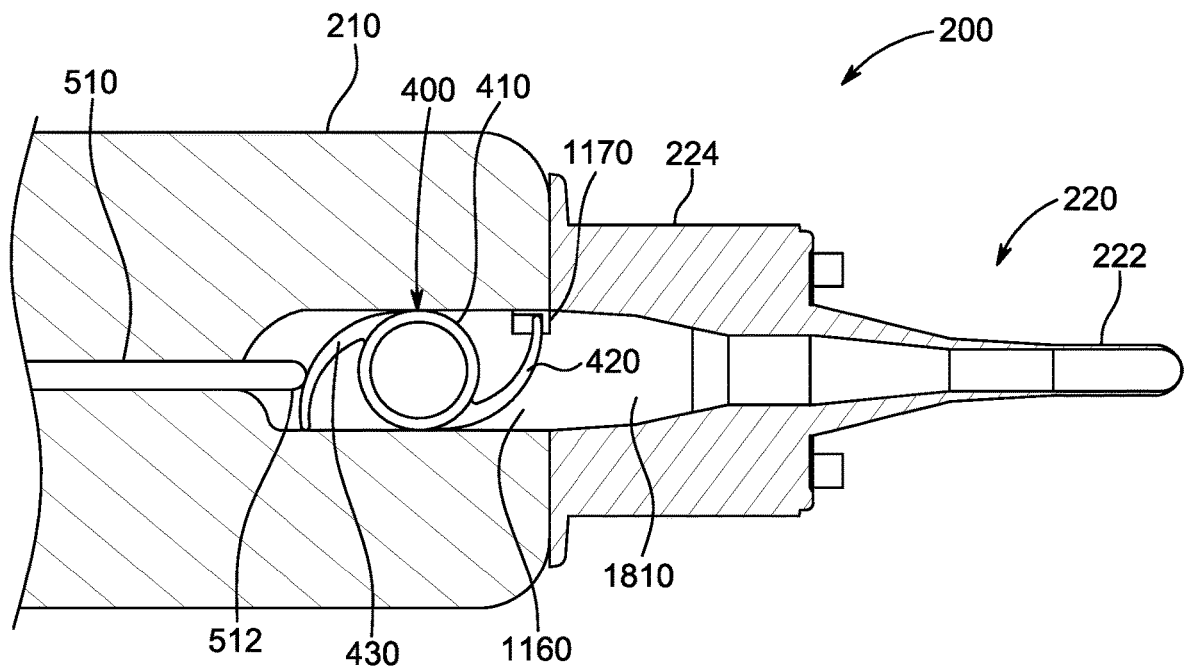
FIG. 18A is a diagram illustrating the operation of the system of FIG. 2B, according to aspects of the disclosure.
Figure 18B:
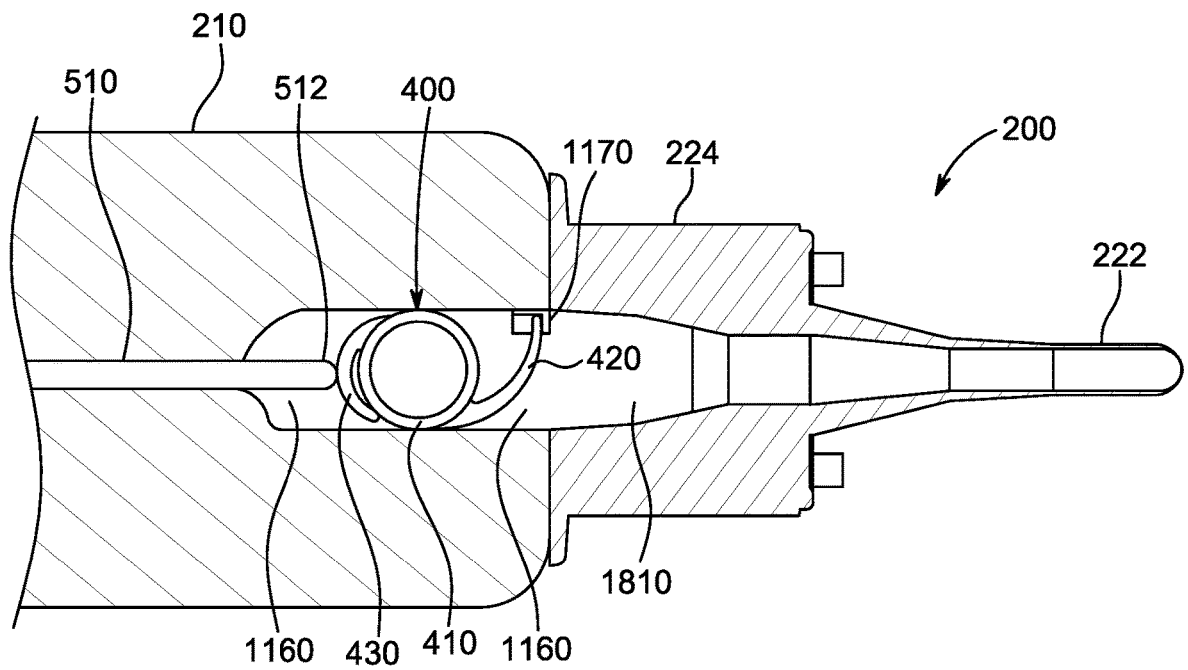
FIG. 18B is a diagram illustrating the operation of the system of FIG. 2B, according to aspects of the disclosure.
Figure 18C:
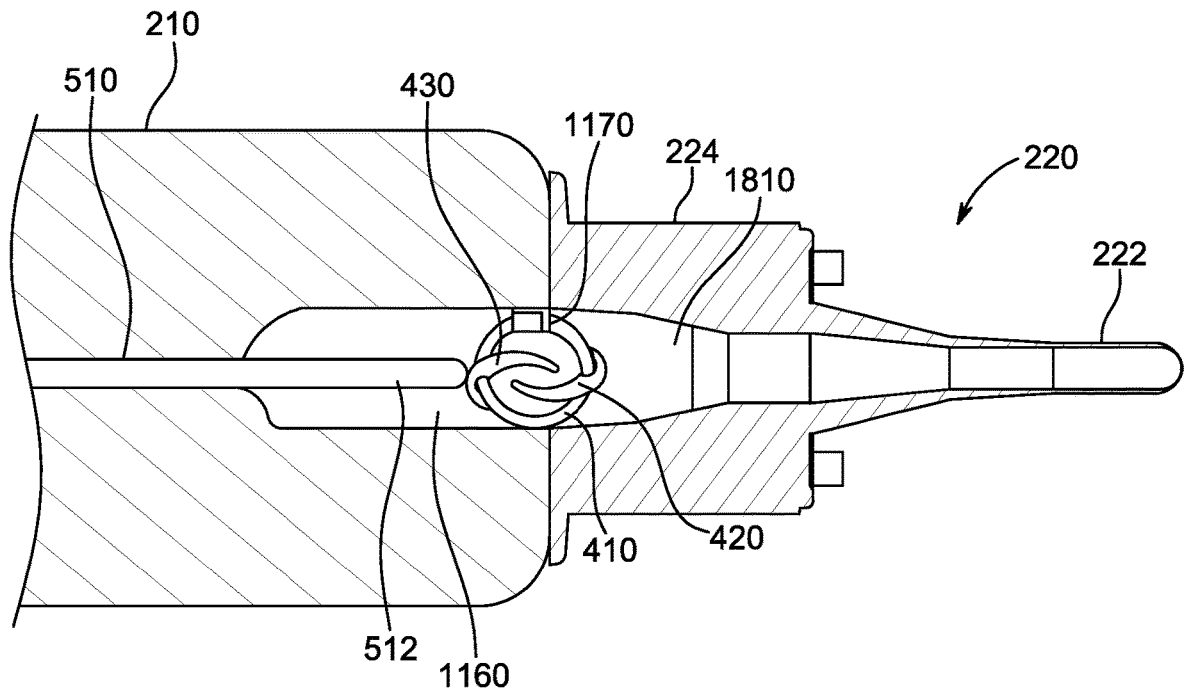
FIG. 18C is a diagram illustrating the operation of the system of FIG. 2B, according to aspects of the disclosure.

FIGS. 18A-D are partial schematic cross-sectional views of the delivery unit 200, when viewed from above, which show the transformations of shape undergone by the IOL 400 when the plunger 180 is depressed to eject the IOL 400 from the delivery unit 200. FIG. 18A, in particular, illustrates the storage position of the IOL 400 inside the lens holder 210. As noted above, when the IOL 400 is in the storage position, the body 410 of the IOL 400 is rested on the ledge 1162, the end of the lead haptic 420 is disposed on the lead haptic shelf 1170, and the end of the trailing haptic 430 is disposed on the trailing haptic shelf 1180 (not shown in FIGS. 18A-D). Now, with reference to FIG. 18B, when plunger 180 is depressed, the pushrod head 514 is disengaged from the retention nut 174. As the pushrod 510 moves along, the flat surface 890 of the tip 512 of the pushrod 500 pushes the trailing haptic 430 causing it to fold over the body 410 of the IOL. After the trailing haptic 430 is folded over the body 410 of the IOL 400, the fork 870 of the pushrod 510 engages the edge of the body 410 of the IOL As seen in FIG. 18C, as the pushrod 510 continues to move along, it pushes the body 410 of the IOL 400, while also causing the lead haptic 420 to press against the sidewall 1820 of the lead haptic shelf 1170, and eventually fold as a result. As the pushrod 510 continues to apply pressure on the IOL 400, the IOL 400 begins to rotate. Concurrently with the rotation of the IOL 400, the lead haptic 420 is folded over the body 410 of the IOL 400 and the IOL 400 travels underneath the lead haptic shelf 1170. After the IOL 400 passes under the lead haptic shelf 1170, it enters a loading chamber 1810 of the cartridge 220.

Figure 18D:
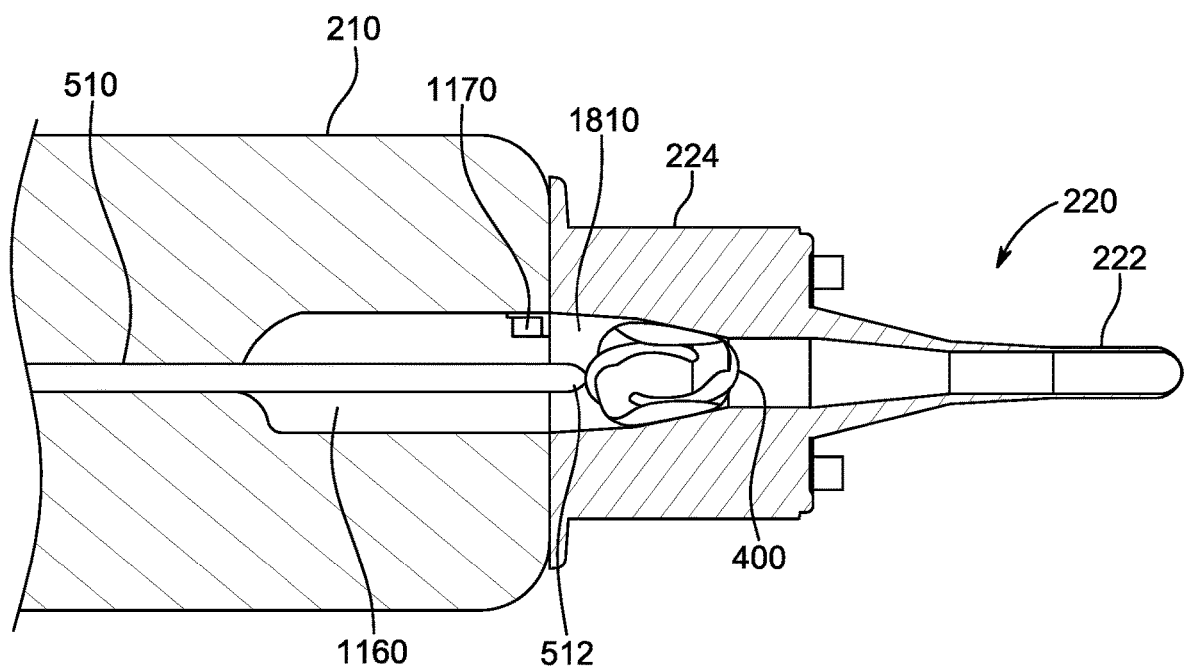
FIG. 18D is a diagram illustrating the operation of the system of FIG. 2B, according to aspects of the disclosure.

FIG. 18D shows the IOL 400 after it has been transferred into the loading chamber 1810 of the cartridge 220. The size of the loading chamber 1810 is desirably smaller than the diameter of the body 410, and therefore acts on and causes the body 410 to curl upward into a "taco" shape. The transition of the body 410 from its original planar configuration to a curled configuration prevents the haptics 420 and 430 from elastically rebounding back to their original positions. In other words, the haptics 420 and 430 are captured over the top of the body 410 by its curled configuration. In this shape, the IOL 400 can be inserted into the eye of a patient. Importantly, when the body 410 is curled up, its overall footprint is reduced, which permits the use of a smaller incision into the patient's eye to insert the IOL 400.

Figure 19:
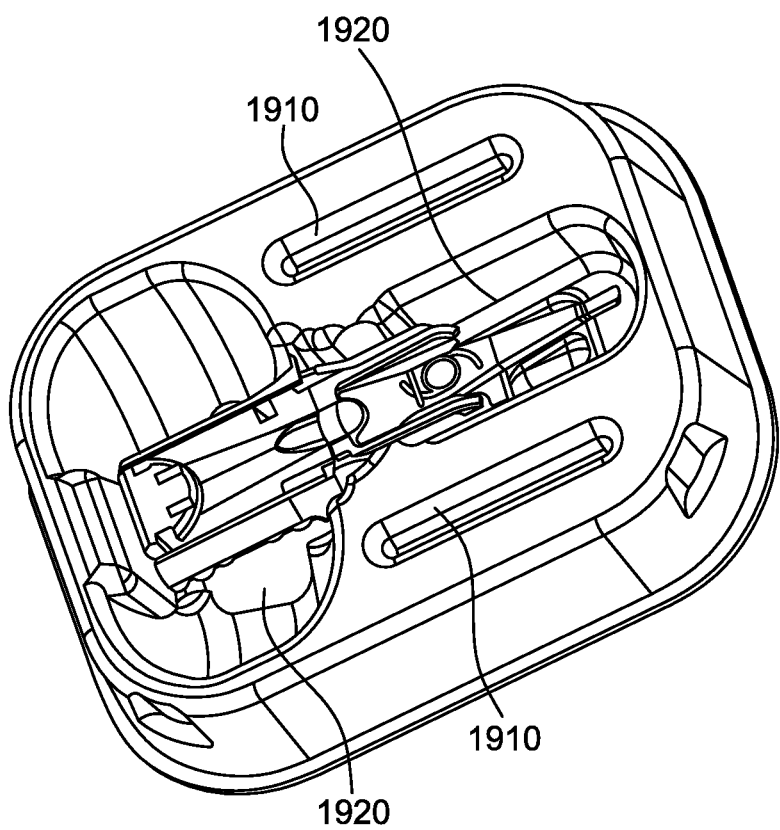
FIG. 19 is a perspective side view of a storage tray of the system of FIG. 2B, according to aspects of the disclosure.

FIG. 19 is a diagram illustrating an example of a storage tray 1900 for storing the delivery unit 200. As illustrated, the storage tray includes ribs 1910 that are arranged to provide extra structural support to the tray and a well 1920 arranged to receive the delivery unit 200. When the delivery unit 200 is disposed into storage tray 1900, the well 1920 may be flooded with BSS to keep the IOL inside the delivery unit 200 hydrated. As noted above, in some implementations, while the delivery unit 200 is disposed in the storage tray 1900, the BSS may enter the delivery unit 200 through the port 1310.

The above-described design opens new opportunities for marketing and using intraocular lens (IOL) implants. Specifically, the design permits IOL implants to be pre-packaged in a delivery unit (e.g., the delivery unit 200) and sold separately from any particular IOL insertion handpiece. The pre-packaging may be performed by the manufacturer, before the IOL implants are sold to hospitals and other medical facilities. Under this arrangement, IOL implants need not be directly handled by medical personnel after they leave the manufacturer's premises. Rather, medical personnel may simply mount a delivery unit containing a pre-loaded IOL onto a selected IOL insertion handpiece, and use the selected handpiece to implant the IOL in a well-known fashion.

The delivery unit may be universally compatible with many different IOL insertion handpieces (e.g., the handpiece 110 and the handpiece 150), thereby giving ophthalmologists the freedom to select a handpiece of their own choosing. Ophthalmologists very often have specific preferences with respect to the IOL insertion handpiece they use. For example, some ophthalmologists may prefer handpieces that are heavier, while other may prefer handpieces that are lighter. As another example, some ophthalmologists may prefer handpieces that are larger, while other may prefer handpieces that are smaller. As another example, some ophthalmologists may prefer to squeeze the plunger of the handpiece during the final stages of the implantation, while others may prefer to twist it. These preferences may often be dictated by the ophthalmologists' physical strength, physical size, and/or motor skills. Accordingly, providing ophthalmologists with the handpiece they prefer may enable to ophthalmologists to operate with greater precision.

Furthermore, ophthalmologists may often have preferences for a specific IOL. However, many IOL insertion systems that are available on the market require the use of the respective IOL insertion handpiece that is part of each system. Thus, if a given ophthalmologist prefers to use IOL implants that are produced by one manufacturer/producer and an IOL insertion handpiece that is produced by another manufacturer/producer, the given ophthalmologist may be not be able to do so, as the preferred IOL implant may not be readily transferable to the preferred handpiece. In other words, the given ophthalmologist may be forced to choose one or the other of her/his preferred IOL insertion handpiece and IOL implant.

By contrast, in some instances, the modular nature of the above-described design may permit ophthalmologists to mix-and-match a given pre-loaded IOL delivery unit with various compatible IOL insertion handpieces that might be available on the market. More specifically, the above-described system permits ophthalmologists to find the IOL handpiece that works best and use only that handpiece, while obtaining additional IOL delivery unit refills as they go. The IOL insertion handpiece and the delivery units may be produced by the same manufacturer/producer or by different manufacturers/producers.

Figure 20:
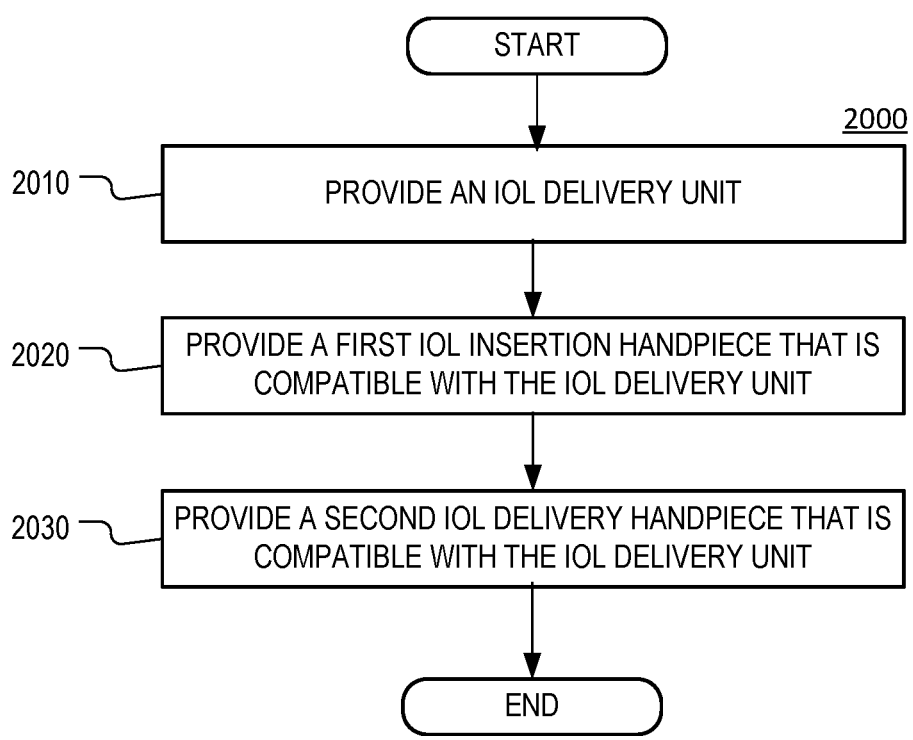
FIG. 20 is a flowchart of an example of a process, according to aspects of the disclosure.

FIG. 20 is a flowchart of an example of process 2000 for selling IOL implants, according to the aspects of the disclosure. At step 2010, an IOL delivery unit is provided that includes a mounting interface for affixing the delivery unit to a compatible handpiece. In some instances, the IOL delivery unit may be the same or similar to the delivery unit 200. Additionally or alternatively, in some instances, the mounting interface may include one or more of cartridge wing portions (e.g., wing portions 224) which are configured to engage retention hooks (e.g., hooks 126 or hooks 166) that are provided on the compatible handpiece. Additionally or alternatively, in some implementations, the mounting interface may include a recess (e.g., recess 214) that is configured to receive one or more coupling elements (e.g., holding base 164, holding base 124, latches 128, and/or latches 168) that are provided on the compatible handpiece. Additionally or alternatively, in some implementations, the mounting interface may include coupling elements (e.g., latches 212) configured to mate with corresponding coupling elements (e.g., latches 168) that are provided on the compatible handpiece.

At step 2020, a first IOL insertion handpiece is provided that is compatible with the IOL delivery unit. In some instances, the first compatible piece may be the same or similar to the handpiece 110. At step 2030, a second IOL insertion handpiece is provided that is compatible with the IOL delivery unit. In some instances, the second compatible handpiece may be the same or similar to the handpiece 150. According to aspects of the disclosure, each of the first IOL insertion handpiece and the second IOL insertion handpiece may have a respective receiving interface for receiving the mounting interface of the IOL delivery unit provided at step 2010. In the present example, the receiving interface of the first IOL insertion handpiece may be the same or similar to the cradle 120. Furthermore, the receiving interface of the second IOL insertion handpiece may be the same or similar to the cradle 160.

According to aspects of the disclosure, a handpiece is compatible with the IOL delivery unit when the IOL delivery unit may be mounted on the handpiece in a manner in which permits the implantation of an IOL contained within the IOL delivery unit. Although in the examples provided above a system of hooks and latches is used to affix the delivery unit 200 to one of the handpiece 110 and the handpiece 150, the present disclosure is not limited to this type of arrangement. In this regard, it will be understood that any other suitable interface for affixing the delivery unit to the first and second handpieces may be used instead. Similarly, it will be understood that any other suitable receiving interface for affixing the delivery unit to the first and second handpieces may be used, as well.

According to aspects of the disclosure, the first handpiece and the second handpiece may differ from one another in at least one of: (i) weight, (ii) length of barrel, (iii) type of plunger, (iv) type of material used to make the handpieces, (v) overall length of the handpieces, and/or (vi) reusability.

For example, in some instances, the two handpieces may have different respective weights. Additionally or alternatively, the respective barrels of the first and second handpieces may have different lengths. Additionally or alternatively, in some instances, the two handpieces may include different plungers. More particularly, the first handpiece may include a plunger which has no threads formed on it, and the second handpiece may have a threaded plunger (e.g., plunger 182). As noted above, having threads on the plunger may permit ophthalmologists to use a twisting motion to drive the IOL during the final stages of its implantation. Additionally or alternatively, in some instances, the two handpieces may be made, at least in part, of different materials; more particularly, the first handpiece may include one or more plastic components, whereas the second handpiece may include only metal components. Additionally or alternatively, in some instances, the two handpieces may have different overall lengths. Additionally or alternatively, in some instances, the first handpiece may be disposable and the second handpiece may be reusable.

According to aspects of the disclosure, providing the pre-loaded delivery unit may include selling the delivery unit. Providing the first handpiece may include one of selling the first handpiece or giving the first handpiece away for free and/or at a reduced cost. Providing the second handpiece may include one of selling the second handpiece or giving the second handpiece away for free and/or at a reduced cost. Any of the pre-loaded delivery unit, the first handpiece, and the second handpiece may be sold via an online storefront, a brick-and-mortar storefront, a catalog, and/or any other suitable method for selling supplies to hospitals and medical professionals.

According to aspects of the disclosure, in some instances, the pre-loaded IOL delivery unit may be provided separately from any of the first handpiece and the second handpiece. For example, the pre-loaded IOL delivery unit may be packaged separately from each of the first handpiece and the second handpiece. As another example, the pre-loaded IOL delivery unit may be sold by itself (or together with other delivery units), without an accompanying IOL insertion handpiece. As another example, the pre-loaded IOL delivery unit may be provided before and/or after any of the first handpiece and the second handpiece is provided According to aspects of the disclosure, in some instances, the pre-loaded IOL delivery unit and at least one of the first handpiece and the second handpiece may be provided in the same kit. For example, the pre-loaded IOL delivery unit and at least one of the first handpiece and the second handpiece may be provided in the same carrying case. In addition, the kit may include other supplies and consumables, such as a bottle of balanced salt solution, etc.

According to aspects of the disclosure, in some instances, the first IOL insertion handpiece and the second IOL insertion handpiece may be produced by different producers. For example, the first handpiece may be produced by a first producer and the second handpiece may be produced by a second producer. Additionally or alternatively, the first producer and the second producer may use different brand names. Additionally or alternatively, the first producer and the second producer may be separately owned. Additionally or alternatively, the first producer and the second producer may share the same manufacturing facility or they may use separate manufacturing facilities.

FIGS. 1A-20 are provided as an example only. At least some of the elements discussed with respect to these figures can be arranged in different order, combined, and/or altogether omitted. It will be understood that the provision of the examples described herein, as well as clauses phrased as "such as," "e.g.", "including", "in some aspects," "in some implementations," and the like should not be interpreted as limiting the disclosed subject matter to the specific examples.

Having described the invention in detail, those skilled in the art will appreciate that, given the present disclosure, modifications may be made to the invention without departing from the spirit of the inventive concepts described herein. Therefore, it is not intended that the scope of the invention be limited to the specific embodiments illustrated and described.

What is being claimed is:

1. A kit for inserting an intraocular lens (IOL), the kit comprising:
    an IOL delivery unit including a pre-loaded IOL and a mounting interface;
    a first IOL insertion handpiece including a first receiving interface configured to receive the IOL delivery unit, and a first insertion assembly configured to push the IOL for inserting the IOL when the first insertion assembly is actuated; and
    a second IOL insertion handpiece including a second receiving interface configured to receive the IOL delivery unit, and a second insertion assembly configured to push the IOL for inserting the IOL when the second insertion assembly is actuated;
    wherein the IOL delivery unit is configured to be selectively mounted to:
       the first IOL insertion handpiece via engagement of the mounting interface with the first receiving interface, and
       the second IOL insertion handpiece via engagement of the mounting interface with the second receiving interface;
    wherein the first IOL insertion handpiece and the second IOL insertion handpiece have at least one different characteristic from each other; and
    wherein the first receiving interface has a first profile, and the second receiving interface has a second profile that is different from the first profile.

2. The kit according to claim 1, wherein the first IOL insertion handpiece is configured to be reusable, and the second IOL insertion handpiece is configured to be disposable.

3. The kit according to claim 1, wherein the first IOL insertion handpiece is configured to insert the IOL based on a twisting motion imparted on the first IOL insertion handpiece, and the second IOL insertion handpiece is configured to insert the IOL based on a pushing or squeezing motion imparted on the second IOL insertion handpiece.

4. The kit according to claim 1, wherein the first receiving interface comprises at least one first hook, and the second receiving interface comprises at least one second hook having a different profile than a profile of the at least one first hook.

5. The kit according to claim 4, wherein the mounting interface comprises at least one wing section that is configured to selectively engage with both the at least one first hook and the at least one second hook such that the IOL delivery unit is configured to be selectively mounted with the first IOL insertion handpiece and the second IOL insertion handpiece.

6. The kit according to claim 1, wherein the mounting interface comprises at least one recess, the first receiving interface includes at least one first latch, the second receiving interface includes at least one second latch, and the at least one recess of the mounting interface is configured to selectively engage with both the at least one first latch and the at least one second latch such that the IOL delivery unit is configured to be selectively mounted with the first IOL insertion handpiece and the second IOL insertion handpiece.

7. A method for preparing an intraocular lens (IOL) for implantation, the method comprising:
- pre-loading an IOL into an IOL delivery unit that includes a mounting interface;
- providing:
  - (i) a first IOL insertion handpiece that is compatible with the IOL delivery unit, the first IOL insertion handpiece including a first receiving interface configured to receive the IOL delivery unit, and a first insertion assembly configured to push the IOL for inserting the IOL when the first insertion assembly is actuated; and
  - (ii) a second IOL insertion handpiece including a second receiving interface configured to receive the IOL delivery unit, and a second insertion assembly configured to push the IOL for inserting the IOL when the second insertion assembly is actuated;
- such that the IOL delivery unit is configured to be selectively attachable to:
  - the first IOL insertion handpiece via engagement of the mounting interface with the first receiving interface; and
  - the second IOL insertion handpiece via engagement of the mounting interface with the second receiving interface,
- wherein the first receiving interface has a first profile and the second receiving interface has a second profile that is different from the first profile.

8. The method according to claim 7, wherein the first IOL insertion handpiece is configured to insert the IOL based on a twisting motion imparted on the first IOL insertion handpiece, and the second IOL insertion handpiece is configured to insert the IOL based on a pushing or squeezing motion imparted on the second IOL insertion handpiece.

9. The method according to claim 7, wherein the first receiving interface comprises at least one first hook, and the second receiving interface comprises at least one second hook having a different profile than a profile of the at least one first hook.

10. The method according to claim 9, wherein the mounting interface comprises at least one wing section that is configured to selectively engage with both the at least one first hook and the at least one second hook such that the IOL delivery unit is configured to be selectively mounted with the first IOL insertion handpiece and the second IOL insertion handpiece.

11. The method according to claim 7, wherein the mounting interface comprises at least one recess, the first receiving interface includes at least one first latch, the second receiving interface includes at least one second latch, and the at least one recess of the mounting interface is configured to selectively engage with both the at least one first latch and the at least one second latch such that the IOL delivery unit is configured to be selectively mounted with the first IOL insertion handpiece and the second IOL insertion handpiece.

12. A kit for inserting an intraocular lens (IOL), the kit comprising:
- an IOL delivery unit including a pre-loaded IOL and a mounting interface comprising at least one recess;
- a first IOL insertion handpiece including a first receiving interface configured to receive the IOL delivery unit, and a first insertion assembly configured to push the IOL for inserting the IOL when the first insertion assembly is actuated; and
- a second IOL insertion handpiece including a second receiving interface configured to receive the IOL delivery unit, and a second insertion assembly configured to push the IOL for inserting the IOL when the second insertion assembly is actuated;
- wherein the IOL delivery unit is configured to be selectively mounted to:
  - the first IOL insertion handpiece via engagement of the mounting interface with the first receiving interface comprising at least one first latch and having a first profile, and
  - the second IOL insertion handpiece via engagement of the mounting interface with the second receiving interface comprising at least one second latch and having a second profile that is different from the first profile;
- wherein the first IOL insertion handpiece and the second IOL insertion handpiece have at least one different characteristic from each other; and
- wherein the at least one recess is configured to selectively engage with both the at least one first latch and the at least one second latch such that the IOL delivery unit is configured to be selectively mounted with the first IOL insertion handpiece and the second IOL insertion handpiece.

13. The kit according to claim 12, wherein the first IOL insertion handpiece is configured to be reusable, and the second IOL insertion handpiece is configured to be disposable.

14. The kit according to claim 12, wherein the first IOL insertion handpiece is configured to insert the IOL based on a twisting motion imparted on the first IOL insertion handpiece, and the second IOL insertion handpiece is configured to insert the IOL based on a pushing or squeezing motion imparted on the second IOL insertion handpiece.

* * * * *